(12) United States Patent
Chen et al.

(10) Patent No.: US 8,754,031 B2
(45) Date of Patent: *Jun. 17, 2014

(54) USE OF PROLACTIN RECEPTOR ANTAGONISTS IN COMBINATION WITH AN AGENT THAT INACTIVATES THE HER2/NEU SIGNALING PATHWAY

(75) Inventors: Wen Yuan Chen, Simpsonville, SC (US); Michele Lynn Scotti, Whitehouse Station, NJ (US)

(73) Assignee: Oncolix, Inc., Houston, TX (US)

( * ) Notice: Subject to any disclaimer, the term of this patent is extended or adjusted under 35 U.S.C. 154(b) by 830 days.

This patent is subject to a terminal disclaimer.

(21) Appl. No.: 11/073,927

(22) Filed: Mar. 8, 2005

(65) Prior Publication Data

US 2005/0271626 A1 Dec. 8, 2005

Related U.S. Application Data

(60) Provisional application No. 60/550,326, filed on Mar. 8, 2004.

(51) Int. Cl.
*A61K 38/00* (2006.01)
*A61K 39/395* (2006.01)

(52) U.S. Cl.
USPC .......................................... 514/1.1; 424/130.1

(58) Field of Classification Search
None
See application file for complete search history.

(56) References Cited

U.S. PATENT DOCUMENTS

| 4,064,118 | A | 12/1977 | Wong | |
|---|---|---|---|---|
| 7,115,556 | B2 * | 10/2006 | Chen et al. | 514/2 |
| 2003/0022833 | A1 | 1/2003 | Chen et al. | |
| 2008/0038369 | A1 * | 2/2008 | Clark | 424/643 |

FOREIGN PATENT DOCUMENTS

| EP | 1 398 322 A1 | 3/2004 |
|---|---|---|
| WO | WO 90/02802 | 3/1990 |
| WO | WO 01/45746 A2 | 6/2001 |

OTHER PUBLICATIONS

Bowie, et al. Science, vol. 247: 1306-1310, 1990.*
Lazar, et al. Mol. Cell. Biol., 8(3): 1247-1252, 1988.*
Burgess, et al. J. Cell Biol. 111: 2129-2138, 1990.*
Ngo et al., in"The Protein Folding Problem and Tediary Structure Prediction", 1994, Merz, et al. (ed.), Birkhauser, Boston, MA, pp. 433, and 492-495.*
Scotti et al., Proceedings of the American Association for Cancer Research Annual Meeting, Jul. 2003, 44, pp. 1286.*
Jain, "Barriers to drug delivery in solid tumors", Sci Am. 171(1): 58-65, 1994.*
Gura, "Systems for identifying new drugs are often faulty", Science 278 (5340), 1041-1042, 1997.*
MSNBC News Services, "Mixed results on new cancer drug", Nov. 2000, total pp. 4.*
Thomas et al., Nature Reviews Genetics, 2003, 4: 346-358.*
Thompson, FDA Consumer Magazine, Sep.-Oct. 2000, 19-24.*
Crystal, R.G., Science, vol. 270, Oct. 1995, pp. 404-410.*
Yamauchi et al., J. Biol. Chem., 2000, 275(43): 33937-33944.*
Scotti et al., Breast Cancer Res. Treat., 2008, 111(2): 241-250.*
Akira, Shizuo, "Functional Roles of STAT Family Proteins: Lessons from Knockout Mice," Stem Cells, 1999, pp. 138-146, vol. 17.
Ali et al., "The use of DNA viruses as vectors for gene therapy," Gene Therapy, 1994, pp. 367-384, vol. 1, No. 6.
Berkner, Kathleen L., "Development of Adenovirus Vectors for the Expression of Heterologous Genes," BioTechniques, 1988, pp. 616-629, vol. 6, No. 7.
Bondar, A.A., GenBank Accession No. #X63235, 1991.
Boutin et al., "Identification of a cDNA Encoding a Long Form of Prolactin Receptor in Human Hepatoma and Breast Cancer Cells," Molecular Endocrinology, 1989, pp. 1455-1461, vol. 3, No. 9.
Buckbinder et al., "Expression of the *Xenopus laevis* prolactin and thyrotropin genes during metamorphosis," Proc. Natl. Acad. Sci. USA, May 1993, pp. 3820-3824, vol. 90.
Bursch et al., "Active cell death induced by the anti-estrogens tamoxifen and ICI 164 384 in human mammary carcinoma cells (MCF-7) in culture: the role of autophagy," Carcinogenesis, 1996, pp. 1595-1607, vol. 17, No. 8.
Cepko et al., "Construction and Applications of a Highly Transmissible Murine Retrovirus Shuttle Vector," Cell, Jul. 1984, pp. 1053-1062, vol. 37, No. 4.
Chang et al., Gen Bank Accession No. #X61052, 1991.
Chang et al., GenBank Accession No. #X61049 , 1991.
Chazin et al., "Transformation mediated by the human HER-2 gene independent of the epidermal growth factor receptor," Oncogene, 1992, pp. 1859-1866, vol. 7.
Chen et al., "Amino Acid Residues in the Third α-Helix of Growth Hormone Involved in Growth Promoting Activity," Molecular Endocrinology, 1995, pp. 292-302, vol. 9, No. 3.
Chen et al., "Effects of Streptozotocin Treatment in Growth Hormone (GH) and GH Antagonist Transgenic Mice," Endocrinology, 1995, pp. 660-667, vol. 136, No. 2.
Chen et al., "Functional Antagonism between Endogenous Mouse Growth Hormone (GH) and a GH Analog Results in Dwarf Transgenic Mice," Endocrinology, 1991, pp. 1402-1408, vol. 129, No. 3.
Chen et al., "Glycine 119 of Bovine Growth Hormone is Critical for Growth-Promoting Activity," Molecular Endocrinology, 1991, pp. 1845-1852, vol. 5, No. 12.
Chen et al., "In Vitro and in Vivo Studies of Antagonistic Effects of Human Growth Hormone Analogs," The Journal of Biological Chemistry, Jun. 3, 1994, pp. 15892-15897, vol. 269, No. 22.
Chen et al., "Mutations in the Third α-Helix of Bovine Growth Hormone Dramatically Affect Its Intracellular Distribution in Vitro and Growth Enhancement in Transgenic Mice," The Journal of Biological Chemistry, Feb. 5, 1991, pp. 2252-2258, vol. 266, No. 4.

(Continued)

*Primary Examiner* — Hong Sang
(74) *Attorney, Agent, or Firm* — Morgan Lewis & Bockius LLP

(57) ABSTRACT

The present invention describes compositions and methods for inhibiting cell proliferation comprising a prolactin receptor antagonist and an agent that inactivates the HER2/neu signaling pathway, and methods of use thereof.

3 Claims, 6 Drawing Sheets

(56) References Cited

OTHER PUBLICATIONS

Chen et al., "Tamoxifen Induces TGF-β1 Activity and Apoptosis of Human MCF-7 Breast Cancer Cells In Vitro," Journal of Cellular Biochemistry, 1996, pp. 9-17, vol. 61, No. 1.

Ciardiello et al., "A Novel Approach in the Treatment of Cancer: Targeting the Epidermal Growth Factor Receptor," Clinical Cancer Research, Oct. 2001, pp. 2958-2970, vol. 7.

Clark et al., "Effects Of Tyrosine Kinase Inhibitors On The Proliferation Of Human Breast Cancer Cell Lines And Proteins Important In The Ras Signaling Pathway," Int. J. Cancer, 1996, pp. 186-191, vol. 65.

Cooke et al., "Human Prolactin cDNA Structural Analysis And Evolutionary Comparisons," The Journal of Biological Chemistry, Apr. 25, 1981, pp. 4007-4016, vol. 256, No. 8.

Cooke et al., "Structure of Cloned DNA Complementary to Rat Prolactin Messenger RNA," The Journal of Biological Chemistry, Jul. 10, 1980, pp. 6502-6510, vol. 255, No. 13.

D'Souza et al., "Overexpression if ERBB2 in human mammary epithelial cells signals inhibition of transcription of the E-cadherin gene," Proc. Natl. Acad. Sci. USA, Jul. 1994, pp. 7202-7206, vol. 91.

Fendly et al., "Characterzation of Murine Monoclonal Antibodies Reactive to Either the Human Epidermal Growth Factor Receptor or HER2/*neu* Gene Product," Cancer Research. Mar. 1, 1990, pp. 1550-1558, vol. 50. No. 5.

Fernandez et al., "Quantitative Determination of Growth Hormone by Immunoblotting," Analytical Biochemistry, 1990, pp. 268-271, vol. 191.

Forrest, A. Patrick, "Chapter 2—Introduction to Breast Cancer," Biology of Female Cancers, 1997, pp. 31-42.

Garnier, J., "Analysis of the Accuracy and Implications of Simple Methods for Predicting the Secondary Structure of Globular Proteins," J. Mol. Biol., 1978, pp. 97-120, vol. 120, No. 4.

Geller et al., "An efficient deletion mutant packaging system for defective herpes simplex virus vectors: Potential applications to human gene therapy and neuronal physiology," Proc. Natl. Acad. Sci. USA, Nov. 1990, pp. 8950-8954, vol. 87.

Ginsburg et al., "Prolactin Synthesis and Secretion by Human Breast Cancer Cells," Cancer Research, Jun. 15, 1995, pp. 2591-2595, vol. 55, No. 12.

Hanks et al., "Molecular cloning and sequence analysis of putative chicken prolactin cDNA," Journal of Molecular Endocrinology, 1989, pp. 21-30, vol. 2, No. 1.

Harding et al., "Growth Hormone (GH) and a GH Antagonist Promote GH Receptor Dimerization and Internalization," The Journal of Biological Chemistry, Mar. 22, 1996, pp. 6708-6712, vol. 271, No. 12.

Hoffman et al., "Molecular controls of apoptosis: differentiation/growth arrest primary response genes, proto-oncogenes, and tumor suppressor genes as positive & negative modulators," Oncogene, 1994, pp. 1807-1812, vol. 9.

Houghten et al., "Generation and use of synthetic peptide combinatorial libraries for basic research and drug discovery," Nature, Nov. 7, 1991, pp. 84-86, vol. 354.

Jaffee et al., "High Efficiency Gene Transfer into Primary Human Tumor Explaints without Cell Selection," Cancer Research, May 15, 1993, pp. 2221-2226, vol. 53, No. 10.

Janicke et al., "Caspase-3 Is Required for DNA Fragmentation and Morphological Changes Associated with Apoptosis," The Journal of Biological Chemistry, Apr. 17, 1998, pp. 9357-9360, vol. 273, No. 16.

Karatzes et al., "Nucleotide sequence of turkey prolactin," Nucleic Acids Research, 1990, p. 1, vol. 18, No. 10.

Kazansky et al., "Regulation of Mammary Gland Factor/Stat5a During Mammary Gland Development," Molecular Endocrinology, 1995, pp. 1598-1609, vol. 9, No. 11.

Kebers et al., "Induction of Endothelial Cell Apoptosis by Solid Tumor Cells," Experimental Cell Research, 1998, pp. 197-205, vol. 240.

Kelly et al., "Purification, Cloning, and Expression of the Prolactin Receptor," Biology of Reproduction, 1989, pp. 27-32, vol. 40.

Kohmoto et al., "Complete amino acid sequence of mouse prolactin," European Journal of Biochemistry, 1984, pp. 227-237, vol. 138, No. 2.

Kuwana et al., "Cloning and Expression of cDNA for Salmon Prolactin in *Escherichia coli*," Agricultural and Biological Chemistry, 1988, pp. 1033-1039, vol. 52, No. 4.

Lam et al., "A new type of synthetic peptide library for identifying ligand-binding activity," Nature, 1991, vol. 354, No. 6848.

Lehrman et al., "Primary structure of equine pituitary prolactin," Int. J. Peptide & Protein Research, 1988, pp. 544-554, vol. 31.

Li et al., "Primary structure of elephant pituitary prolactin," Int. J. Peptide & Protein Research, 1989, pp. 67-69, vol. 33.

Li et al., "Studies on Pituitary Lactogenic Hormone XXX. The Primary Structure of the Sheep Hormone," Archives of Biochemistry and Biophysics, 1970, pp. 705-737, vol. 141, No. 2.

Li, Choh Hao, "Studies on Pituitary Lactogenic Hormone. The Primary Structure Of The Porcine Hormone," Int. J. Peptide & Protein Research, 1976, pp. 205-224, vol. 8.

Martinat et al., "Determination of the primary and secondary structures of the dromedary (*Camelus dromedarius*) prolactin and comparison with prolactins from other species," Biochimica et Biophysica Acta, 1991, pp. 339-345, vol. 1077, No. 3.

Mercier et al., "Rainbow Trout Prolactin cDNA Cloning in *Escherichia coli*," DNA, 1989, pp. 119-125, vol. 8, No. 2.

Miles, David W., "Update on HER-2 as a target for cancer therapy Herceptin in the clinical setting," Breast Cancer Research, 2001, pp. 380-384, vol. 3, No. 6.

Miller and Langdon, "Chapter 3—Hormonal, Growth Factor, and Cytokine Control of Breast Cancer," Biology of Female Cancers, 1997, pp. 43-60.

Milleret al., "Cloning Of DNA Complementary To Bovine Prolactin mRNA," Endocrinology, 1980, pp. 851-854, vol. 107, No. 3.

Muro-Cacho et al., "Gene Transfer in Human Lymphocytes Using a Vector Based on Adeno-Associated Virus," Journal of Immunotherapy, 1992, pp. 231-237, vol. 11, No. 4.

Noso et al., "Isolation and characterization of glycosylated and non-glycosylated prolactins from alligator and crocodile," Int. J. Peptide & Protein Research, 1992, pp. 250-257, vol. 39.

Olayioye, Monilola A., "Review—Update on HER-2 as a target for cancer therapy Intracellular signaling pathways of ErbB2/HER-2 and family members," Breast Cancer Research, 2001, pp. 385-389, vol. 3.

Pääbo et al., "Structural and functional dissection of an MHC class I antigen-binding adenovirus glycoprotein," The EMBO Journal, 1986, pp. 1921-1927, vol. 5, No. 8.

Peirce et al., "Quantification of prolactin receptor mRNA in multiple human tissues and cancer cell lines by real time RT-PCR," Journal of Endocrinology, Aug. 28, 2001, pp. R1-R4, vol. 171.

Rentier-Delrue et al., "Tilapia Prolactin: Molecular Cloning of Two cDNAs and Expression in *Escherichia coli*," DNA, A Journal of Molecular and Cellular Biology, 1989, pp. 261-270, vol. 8, No. 4.

Roberts et al., "Chemistry for peptide and protein PEGylation," Advanced Drug Delivery Reviews, 2002, pp. 459-476, vol. 54.

Ross et al., Encyclopedia Reference of Cancer, 2001, pp. 401-403.

Roy et al., "The Topoisomerase II Inhibitor Teniposide (VM-26) Induces Apoptosis in Unstimulated Mature Murine Lymphocytes," Experimental Cell Research, 1992, pp. 416-424, vol. 200.

Saiga et al., GenBank Accession No. 13032, 1988.

Sasavage et al., "Nucleotide Sequence of Bovine Prolactin Messenger RNA—Evidence For Sequence Polymorphism," The Journal of Biological Chemistry, Jan. 25, 1982, pp. 678-681, vol. 257, No. 2.

Shawver et al., "Smart drugs: Tyrosine kinase inhibitors in cancer therapy," Cancer Cell, Mar. 2002, pp. 117-123, vol. 1.

Sherwood et al., "Cell Cycle Analysis of Apoptosis Using Flow Cytometry," Methods in Cell Biology, 1995, Chapter 5, vol. 46, pp. 77-97.

Slamon et al., "Human Breast Cancer: Correlation of Relapse and Survival with Amplification of the HER-2/*neu* Oncogene," Science, Jan. 9, 1987, pp. 177-182, vol. 235.

Song et al., "Molecular cloning and expression of salmon prolactin cDNA," Eur. J. Biochem., 1988, pp. 279-285, vol. 172.

Songyang et al., "SH2 Domains Recognize Specific Phosphopeptide Sequences," Cell, Mar. 12, 1993, pp. 767-778, vol. 72.

(56) References Cited

OTHER PUBLICATIONS

Steller, Hermann, "Mechanisms and Genes of Cellular Suicide," Science, Mar. 10, 1995, pp. 1445-1449, vol. 267.

Stern, David F., "Tyrosine kinase signalling in breast cancer ErbB family receptor tyrosine Kinases," Breast Cancer Research, 2000, pp. 176-183, vol. 2, No. 3.

Sutter et al., "Nonreplicating vaccinia vector efficiently expresses recombinant genes," Proc. Natl. Acad Scl. USA, Nov. 1992, pp. 10847-10851, vol. 89.

Takahashi et al., "Molecular cloning and nucleotide sequence analysis of complementary DNA for bullfrog prolactin," Journal of Molecular Endocrinology, 1990, pp. 281-287, vol. 5, No. 3.

Tsubokawa et al., "Primary structure of fin whale prolactin," Int. J. Peptide & Protein Research, 1985, pp. 442-448, vol. 25, No. 4.

Van Engeland et al., "A Novel Assay to Measure Loss of Plasma Membrane Asymmetry During Apoptosis of Adherent Cells in Culture," Cytometry, 1996, pp. 131-139, vol. 24, No. 2.

Vogel et al., "Efficacy and Safety of Trastuzumab as a Single Agent in First-Line Treatment of HER2-Overexpressing Metastatic Breast Cancer," Journal of Clinical Oncology, Feb. 1, 2002, pp. 719-726, vol. 20, No. 3.

Wakao et al., "Mammary gland factor (MGF) is a novel member of the cytokine regulated transcription factor gene family and confers the prolactin response," The EMBO Journal, 1994, pp. 2182-2191, vol. 13, No. 9.

Wang et al., "Growth hormone (GH) indices tyrosine-phosphorylated proteins in mouse L cells that express recombinant GH receptors," Proc. Natl. Acad. Sci. USA, Feb. 1994, pp. 1391-1395, vol. 91.

Wang et al., "Second-generation adenovirus vectors," Natural Medicine, Jun. 1996, pp. 714-716, vol. 2, No. 6.

Watahiki et al., "Primary Structure of Chicken Pituitary Prolactin Deduced from the cDNA Sequence," The Journal of Biological Chemistry, Apr. 5, 1989, pp. 5535-5539, vol. 264, No. 10.

Waxman et al., "Intermittent Plasma Growth Hormone Triggers Tyrosine Phosphorylation and Nuclear Translocation of a Liver-Expressed, Stat 5-related DNA Binding Protein," The Journal of Biological Chemistry, Jun. 2, 1995, pp. 13262-13270, vol. 270, No. 22.

Wuerzberger et al., "Induction of Apoptosis in MCF-7:WS8 Breast Cancer Cells by β-Lapachone," Cancer Research, May 1, 1998, pp. 1876-1885, vol. 58, No. 9.

Wyllie, A.H., "Cell Death: The Significance of Apoptosis," International Review of Cytology, 1980, pp. 251-306, vol. 68.

Wyllie, A.H., "Glucocorticoid-induced thymocyte apoptosis is associated with endogenous endonuclease activation," Nature, Apr. 10, 1980, p. 555, vol. 284, No. 5756.

Yakes et al., "Herceptin-induced Inhibition of Phosphatidylinositol-3 Kinase and Akt Is Required for Antibody-mediated Effects on p27, Cyclin D1, and Antitumor Action," Cancer Research, Jul. 15, 2002, pp. 4132-4141, vol. 62.

Yamaguchi et al., "Complete Amino Acid Sequences of a Pair of Fish (Tilapia) Prolactins, $tPRL_{177}$ and $tPRL_{188}$," The Journal of Biological Chemistry, Jul. 5, 1988, pp. 9113-9121, vol. 263, No. 19.

Yamauchi et al., "Constitutive Tyrosine Phosphorylation of ErbB-2 via Jak2 by Autocrine Secretion of Prolactin in Human Breast Cancer," The Journal of Biological Chemistry, Oct. 27, 2000, pp. 33937-33944, vol. 275, No. 43.

Yasuda et al., "Primary Structure of Chum Salmon Prolactins: Occurrence of Highly Conserved Regions," Archives of Biochemistry and Biophysics, Feb. 1, 1986, pp. 528-541, vol. 244, No. 2.

Yasuda et al., "Primary Structure of Common Carp Prolactins," General and Comparative Endocrinology, 1987, pp. 280-290, vol. 66.

Yasuda et al., "The Complete Amino Acid Sequence of Prolactin from the Sea Turtle (*Chelonia mydas*)," General and Comparative Endocrinology, 1990, pp. 363-371, vol. 80.

Zufferey et al., "Multiply attenuated lentiviral vector achieves efficient gene deliver in vivo," Nature Biotechnology, Sep. 1997, pp. 871-875, vol. 15.

Chen et al. In Vitro and in Vivo Studies of Antagonistic Effects of Human Growth Hormone Analogs. J. Bio. Chem. 1994. vol. 269, pp. 15892-15897.

* cited by examiner

SEQUENCE LISTING

```
<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gcttagcagt tgttgttgtg                                                    20

<210> SEQ ID NO 2
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
atgaacatca aaggat                                                        16

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
cggctcctag agaggatgga gct                                                23

<210> SEQ ID NO 4
<211> LENGTH: 24
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 4
gcacttcagt atccatggtc tggt                                             24

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
agaaggcagc caacatgaag                                                  20

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      6-His tag

<400> SEQUENCE: 6

His His His His His His
  1               5
```

USE OF PROLACTIN RECEPTOR ANTAGONISTS IN COMBINATION WITH AN AGENT THAT INACTIVATES THE HER2/NEU SIGNALING PATHWAY

This application claims the benefit of priority from U.S. provisional application 60/550,326, filed on Mar. 8, 2004, incorporated herein by reference.

BACKGROUND

1. Field of the Invention

The present invention relates to compositions and methods for treating cancer. In particular, the invention describes the use of a prolactin receptor antagonist in combination with an agent that inactivates the HER2/neu signaling pathway.

2. Background of the Invention

Breast cancer is the second leading cause of cancer death in women in Western society. While the cause of breast cancer is still not clear, it is generally believed that tumorigenesis is not triggered by a single etiologic agent. Instead, the genesis of breast cancer is a result of accumulated damage to cells within the breast over many years.

For decades, the primary therapies for women with breast cancer have been surgery, radiation, or a combination of the two (Miller and Langdon, BIOLOGY OF FEMALE CANCERS, CRC Press LLC, pp 43-60 (1997); Forrest, BIOLOGY OF FEMALE CANCERS, CRC Press LLC, pp 31-42 (1997)). Hormone therapy and chemotherapy are common treatments for breast cancer. But because of the heterogeneous nature of the cancer, there is a low response rate to many therapies. For example, approximately half of the cancers in the breast are estrogen receptor (ER) negative and therefore will not respond to tamoxifen (Forrest, supra).

Recently, novel agents have been designed to target oncogene products such as HER2. HER2 is located on chromosome band 17821.1 and encodes a transmembrane receptor tyrosine kinase (Ross et al., ENCYCLOPEDIC REFERENCE OF CANCER, pp. 401-3, Springer, 2001). The name HER2 is derived from Human Epidermal growth factor Receptor" as it features substantial homology with EGFR (id.). Heterodimerization of HER2 with other ErbB family members is initiated through ligand binding, and leads to autophosphorylation, transphosphorylation, and finally activation of a receptor dimer that acts as a kinase for cytoplasmic substrates (Stern, D F, Breast Cancer Res. 2:176-83 (2000).

Overexpression of the HER2 protein occurs in 25% to 30% of human breast cancers and leads to a particularly aggressive form of the disease (Ciardiello et al., Clin. Cancer Res. 7:2958-70 (2001); Miles D W, Breast Cancer Res., 3:380-84 (2001); Shawver et al., Cancer Cell, 1:117-123 (2002); Vogel et al., J. Clin. Oncol., 20:719-26 (2002)). Women whose cancer overexpresses HER2 have a poor prognosis, with a median survival of 3 years (compared to 6-7 years in HER-2 negative cases) (Slamon et al., Science 235:177-82 (1987); Chazin et al., Oncogene, 7:1859-66 (1992)). Thus, HER2 became an important target in developing chemotherapeutic agents.

HERCEPTIN® (Trastuzamab; Genentech, San Francisco, Calif.) is a humanized monoclonal antibody directed to the HER2 ectodomain and is believed to block and neutralize HER2 protein (Fendly et al., Cancer Res. 50:1550-58 (1990)). HERCEPTIN® (trastuzamab) was approved in 1998 for clinical use in HER2 overexpressing metastatic breast cancer. Recent data indicated that HERCEPTIN® (trastuzamab) has anti-tumor activity as a single agent used in a phase II clinical trial of heavily pre-treated patients with advanced breast cancer. In addition, use of HERCEPTIN® (trastuzamab) in conjunction with chemotherapy was associated with higher response rates, longer time to progression and improved survival when compared with chemotherapy alone. But despite encouraging clinical data, the overall response rate for HERCEPTIN® (trastuzamab) as a single agent is 20 to 30% (Miles; Vogel; Slamon, supra).

Therefore, there exists a need in the art to identify compositions and methods to effectively treat various cancers, including breast cancer. The present invention describes compounds that act synergistically with HERCEPTIN® (trastuzamab) to treat breast and other cancers.

SUMMARY OF THE INVENTION

The present invention describes compositions and methods for inhibiting cell proliferation, inducing apoptosis in a cell, or slowing tumor growth comprising exposing a target cell to a prolactin variant/prolactin receptor antagonist and an agent that inactivates the HER2/neu signaling pathway. In a preferred embodiment, the prolactin receptor antagonist comprises prolactin with an amino acid substitution at position 129 and the agent that inactivates the HER2/neu signaling pathway is an agent that blocks HER2/neu. In some embodiments, the agent that blocks HER2/neu is a humanized monoclonal antibody. More preferably, the humanized monoclonal antibody is HERCEPTIN® (trastuzamab) and is administered either concurrently or sequentially with the prolactin receptor antagonist. Also preferred, the amino acid at position 129 in the prolactin receptor antagonist has been substituted to become arginine. The methods and compositions described herein can be used to treat cancer, such as breast or prostate cancer.

DETAILED DESCRIPTION OF THE INVENTION

Figure 1:
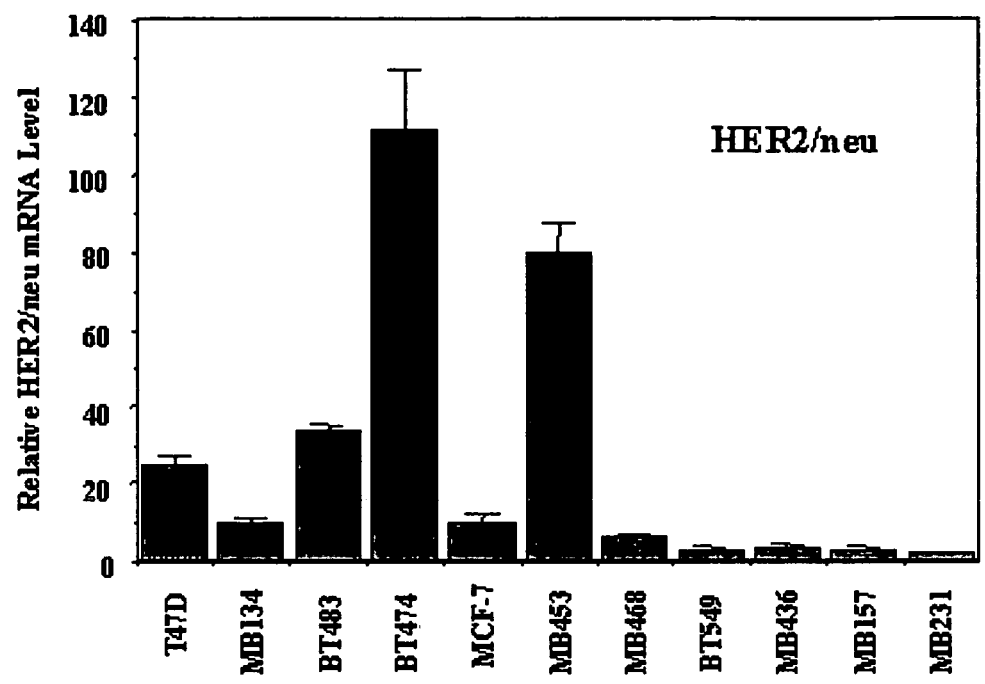
FIG. 1. Comparison of relative HER2 mRNA levels in eleven breast cancer cell lines and normal breast tissue, normalized to 100 ng of 3-actin RNA. Y-axis describes the fold difference.

In recent studies, it has been reported that the autocrirte/paracrine secretion of human prolactin (hPRL) in breast cancer cells stimulates tyrosine phosphorylation of HER2 (via activation of JAK2). Therefore, the prolactin signaling pathway may be implicated in constitutively phosphorylating tyrosine residues in HER2 (Yamauchi et al., *J. Biol. Chem.*, 275:33937-44 (2000)). Indeed, clinical data demonstrated that there is a strong correlation between PRL expression and proliferative and metastatic activity in HER2 positive breast cancer patients (id.). Also, the activation of either HER2 or PRLR lead to the activation of RAS/RAF and the MAPK pathway (Yakes et al., *Cancer Res.*, 62:4132-41 (2002); Olayioye M A. *Breast Cancer Res.*, 3:385-89 (2001)), indicating that there may be some cross-talk between HER2 and PRL signaling pathways.

Previously, the inventors developed a hPRLR antagonist, G129R. G129R is prolactin with a single amino acid substation; the glycine at position 129 of the native sequence is replaced with an arginine. G129R has anti-tumor effects in cultured human breast cancer cells and in nude mouse models. The inventors have also previously demonstrated that G129R acts by inhibiting JAK2/STAT/MAPK phosphorylation and therefore leads to the down regulation of Bcl-2 expression. G129R also inhibits the Akt signaling pathway. Importantly, preclinical data indicates that G129R is safe in animals, including mice and rabbits, even at high doses.

Without wishing to be bound to any theory, the inventors believe that overexpressed HER2 in breast cancer cells is already phosphorylated, pointing to the oncogenic potential of HER2 (D'souza et al., *Proc. Natl. Acad. Sci. USA*, 91:7202-6 (1994); Clark et al., *Int. J. Cancer.*, 65:186-91 (1996)). By administering a prolactin receptor antagonist, HER2 is directly inactivated through dephosphorylation. It is also thought that G129R inhibits MAPK activity through PRLR. The combination of G129R with HERCEPTIN® (trastuzamab) synergistically interferes with cancer cell proliferation.

The term prolactin (PRL) refers herein to human and non-human animal forms of the hormone prolactin. Such prolactins include, but are not limited to, prolactins for which the amino acid sequences are set forth in Cooke et al., *J. Biol. Chem.*, 256:4007 (1981); Cooke et al., *J. Biol. Chem.*, 225: 6502 (1980); Kohmoto et al., *Eur. J. Biochem.*, 138:227 (1984); Tsubokawa et al., *Int. J. Peptide Protein Res.*, 25:442 (1985); Bondar et al., GenBank Accession No. #X63235 (1991); Sasavage et al., *J. Biol. Chem.* 257:678 (1982); Miller et al., *Endocrinol.* 107:851 (1980); Li et al., *Arch. Biochem. Biophys.* 141:705 (1970); Li, *Int. J. Peptide Protein Res.*, 8:205 (1976); Martinant et al., *Biochem. Biophys. Acta*, 1077: 339 (1991); Lehrman et al., *Int. J. Peptide Protein Res.*, 31:544 (1988); Li et al., Int. J. *Peptide Protein Res.*, 33:67 (1989); Hanks et al., *J. Mol. Endocrinol.*, 2:21 (1989); Watahiki et al., *J. Biol. Chem.*, 264:5535 (1989); Karatzas et al., *Nucl. Acids Res.*, 18:3071 (1990); Yasuda et al., *Gen. Comp. Endocrinol.*, 80:363 (1990); Noso et al., *Int. J. Peptide Protein Res.*, 39:250; Buckbinder et al., *Proc. Natl. Acad. Sci. U.S.A.*, 90:3820 (1993); Takahashi et al., *J. Mol. Endocrinol.*, 5:281; Yamaguchi et al., J. Biol. Chem., 263:9113 (1988); Rentler-Delrue et al., *DNA*, 8:261; Yasuda et al., *Gen. Comp. Endocrinol.*, 66:280 (1987); Chang et al., GenBank Acc. No. #X61049 (1991); Chang et al., GenBank Acc. No. #X61052 (1991); Yasuda et al., *Arch. Biochem. Biophys.*, 244:528 (1986); Kuwana et al., *Agric. Biol. Chem.*, 52:1033 (1988); Song et al., *Eur. J. Biochem.*, 172:279 (1988); Mercier et al., DNA 8:119 (1989).

An agent that inactivates the HER2/neu signaling pathway is any compound that does not bind the prolactin receptor and that affects HER2/neu signaling either at the receptor level or at a downstream signaling molecule. For example, an agent that inactivates the HER2/neu signaling pathway can block HER2/neu or can affect phosphorylation of a signaling molecule downstream of HER2/neu. For example, the agent may be a humanized monoclonal antibody, such as HERCEPTIN® (trastuzamab), a vaccine against the HER2 gene product linked to tetanus toxin fragments, a ribozyme that down regulates the HER2/neu oncogene, such as Herzyme (Ribozyme Pharmaceuticals Inc.), synthetic polyamides designed to inhibit or reduce gene transcription and expression, and the like. Other agents that inactivate the HER2/neu signaling pathway include vaccines, which act to generate antibodies that block HER2/neu signaling. Such vaccines may comprise HER2/neu peptides, proteins, or fragments thereof, or viral vectors or plasmids containing genes encoding Her2/neu peptides, proteins, or fragments thereof. For example, the agent that inactivates the HER2/neu signaling pathway may be a viral vector based vaccine. Such vaccines may be replication defective but are nevertheless able to effectively present an antigen so as to generate an immune response that ultimately blocks HER2/neu signaling. For example, the antigen may be a HER2/neu protein, or fragment thereof, and the immune system mounts an immune response against cells that express the HER2/neu protein.

The term "prolactin variant" or "prolactin receptor antagonist" refers to a form of prolactin that interferes with the prolactin signaling pathway. A preferred prolactin receptor antagonist comprises prolactin with at least one amino acid that has been altered from its naturally occurring sequence by insertion, deletion, and/or substitution of amino acids. The G129R hPRL variant is also referred to herein as hPRLA, the "A" referring to its antagonist activity.

The ability of such a prolactin receptor antagonist to antagonize the action of PRL at its receptor is defined as the ability of the variant to inhibit an effect mediated, under normal conditions, by PRL. For example, where PRL has a proliferative effect on a species of cell, a PRL receptor antagonist according to the invention inhibits the proliferation of the species of cells. Prolactin receptor antagonists are described in published US Patent Application No. 2003 0022833, which is incorporated herein by reference in its entirety.

As a specific non-limiting example, a PRL variant/prolactin receptor antagonist may be identified as an antagonist of PRL by determining the ability of the variant to block the ability of PRL to act via its receptor when both PRL and the PRL variant are present. As an example, where a given concentration X of PRL is associated with an increase Y in the proliferation of cells expressing the PRLR in culture, when a comparable sample of cells are exposed to PRL at concentration X, and a PRL variant at a concentration V, the proliferation of the cells will increase by Z, where Z is less than Y and may be a negative number.

In another example of the invention, the PRL variant/prolactin receptor antagonist is a variant of a naturally occurring human PRL, and has a substitution in a glycine residue at position 129 with another amino acid. The substitution, represented in shorthand form by G129*, where * is a naturally occurring or synthetic amino acid other than glycine, may be the sole variation from the naturally occurring sequence or one of several alterations (including insertions, deletions, and/or substitutions of amino acids). The substituted amino acid may be neutral-polar amino acids such as alanine, valine, leucine, isoleucine, phenylalanine, proline, methionine; neutral non-polar amino acids such as serine, threonine, tyrosine, cysteine, tryptophan, asparagine, glutamine, aspartic acid; acidic amino acids such as aspartic and glutamic acid; and basic amino acids such as arginine, histidine or lysine. In preferred embodiments of the invention, the glycine at position 129 of hPRL may be substituted with valine, leucine, isoleucine, serine, threonine, proline, tyrosine, cysteine, methionine, arginine, histidine, tryptophan, phenylalanine, lysine, asparagine, glutamine, aspartic acid, and glutamic acid. In a most preferred embodiment of the invention, the substitution replaces the glycine at position 129 with arginine (G129R). In yet another embodiment, the present invention provides for a prolactin variant wherein the glycine at position 129 is deleted.

In yet other nonlimiting embodiments, a prolactin variant/prolactin receptor antagonist is linked to another protein as part of a fusion protein. For example, the prolactin variant may be linked to interleukin 2, or the G129R variant of human prolactin is linked to interleukin 2.

The PRL variants/prolactin receptor antagonists of the invention may be prepared by chemical synthesis or by recombinant DNA techniques. Generally, a cDNA of PRL may be prepared using standard PCR amplification techniques, RNA or cDNA prepared from a cell which produces PRL (such as a pituitary cell) as a template, and oligonucleotide primers designed based on known PRL nucleic acid or amino acid sequence. A non-limiting example of the preparation of a cDNA encoding HPRL is set forth in published US Patent Application No. 2003 0022833 (Wagner et al.). Alterations may then be introduced into the PRL cDNA either randomly or by directed mutagenesis. An example of the use of oligonucleotide mediated site-directed mutagenesis is also set forth in published US Patent Application No. 2003 0022833 (Wagner et al.), and illustrates the introduction of the G129R substitution into hPRL.

Where the PRL variant is to be produced by recombinant techniques, a nucleic acid encoding the PRL variant may be incorporated into an expression vector, operatively linked to a suitable promoter/enhancer sequence. The expression vector may further contain one or more elements which aid in the expression of the PRL variant, including a transcription termination site, a polyadenylation site, a ribosome binding site, a signal sequence, etc. Suitable expression systems include mammalian cells, insect cells, plant cells, yeast cells, slime mold, and organisms, including transgenic plants and transgenic animals. Suitable expression vectors include herpes simplex viral based vectors such as pHSV1 (Geller et al., *Proc. Natl. Acad. Sci. U.S.A.* 87:8950-8954 (1990)); retroviral vectors such as MFG (Jaffee et al., *Cancer Res.* 53:2221-2226 (1993)), and in particular Moloney retroviral vectors such as LN, LNSX, LNCX, LXSN (Miller and Rosman, *Biotechniques,* 7:980-989 (1989)); vaccinia viral vectors such as MVA (Sutter and Moss, *Proc. Natl. Acad. Sci. U.S.A.* 89:10847-10851 (1992)); adenovirus vectors such as pJM17 (Ali et al., *Gene Therapy* 1:367-384 (1994); Berker, *Biotechniques* 6:616-624 (1988); Wand and Finer, *Nature Medicine* 2:714-716 (1996)); adeno-associated virus vectors such as AAV/neo (Mora-Cacho et al., *J. Immunother.,* 11:231-237 (1992)); lentivirus vectors (Zufferey et al., *Nature Biotechnology* 15:871-875 (1997)); plasmid vectors such as pcDNA3 and pcDNA1 (InVitrogen), pET 11a, pET3a, pET11d, pET3d, pET22d, and pET12a (Novagen); plasmid AH5 (which contains the SV40 origin and the adenovirus major late promoter), pRC/CMV (InVitrogen), pCMU II (Paabo et al., *EMBO J.,* 5:1921-1927 (1986)), pZipNeo SV (Cepko et al., *Cell,* 37:1053-1062 (1984)), pSR.alpha. (DNAX, Palo Alto, Calif.) and pBK-CMV; and baculovirus expression vectors (O'Reilly et al., BACULOVIRUS EXPRESSION VECTORS, Oxford University Press (1995)), such as p2Bac (InVitrogen).

A PRL variant produced in a recombinant expression system may then be purified by standard techniques, including electrophoresis, chromatography (including affinity chromatography), and ultrafiltration.

Truncated Prolactin Receptors

The present invention provides for cell-free truncated prolactin receptors (referred to herein as PRL-BP(s)), which retain the ability to bind to PRL and therefore are able to compete with the cell surface forms of PRLR for PRL binding, thereby inhibiting the ability of PRL to interact with its receptor.

A PRL-BP may be prepared by removing all or a part of the transmembrane and/or intracellular domains of the PRLR, either enzymatically or using recombinant DNA techniques. In a specific, nonlimiting embodiment of the invention, the PRLR to be truncated is as described in Boutin et al., *Mol. Endocrinol.* 3:1455-1461 (1989).

For recombinant preparation, nucleic acid molecules encoding a naturally occurring prolactin receptor may be prepared and then altered to encode a PRL-BP. For example, but not by way of limitation, the PRLR may be cloned using techniques as set forth in published US Patent Application No. 2003 0022833 (Wagner et al.).

The amino acid sequence of PRLR from a variety of different organisms is known. The human PRLR sequence is obtainable from GenBank Accession No: 13032. Further, the amino acid residues which delineate the extracellular, transmembrane and cytoplasmic domains of the PRLR are also known (see for example, Kelly et al., *Biol. Reprod.,* 40:27-32 (1989)). Given the elucidation of these domains, one skilled in the art would readily be capable of producing a truncated form of PRLR which retains the ability to bind PRL, but which may be used to inhibit the effects of PRL.

Recombinant DNA methods which are well-known to those skilled in the art can be used to construct expression vectors containing PRL-BP coding sequences and appropriate transcriptional/translational control signals. The efficiency of expression can be enhanced by the inclusion of appropriate transcriptional enhancer elements, transcriptional terminators, etc. The methods may include in vitro recombinant DNA and synthetic techniques and in vivo recombinants (See, for example, Sambrook et al., 1989, MOLECULAR CLONING: A LABORATORY MANUAL, Cold Spring Harbor Press, Cold Spring Harbor, N.Y., and Glover, D. M., (ed.), 1985, DNA CLONING: A PRACTICAL APPROACH, MRL Press, LTD., Oxford, U.K., Vol. I, II) which are incorporated by reference herein in their entirety.

When recombinant DNA technology is used to produce PRL-BP, it may be advantageous to engineer fusion proteins that can facilitate, for example, solubility or purification. Such fusion proteins can be made by ligating the appropriate nucleic acid sequences encoding the desired amino acid sequences to each other by methods known in the art, in the proper reading frame, and expressing the fusion protein by methods commonly known in the art. The PRL-BP gene product contained within such fusion proteins can comprise, for example, one or more of the extracellular domains or portions, preferably the ligand-binding portion.

In one specific example, for hPRL-BP expression, a mammalian expression vector such as pcDNA3.1/His Xpress (Invitrogen Corp., San Diego, Calif.) may be used. This vector contains a human immediate-early cytomegalovirus promoter and bGH poly A addition signal. In addition, it offers an in frame $(His)_6$ peptide (SEQ ID No: 6) at the N-terminus which allows an easy detection after purification of hPRL-BP. Recombinant hPRL-BP produced using such a vector in cell culture may be concentrated by ultrafiltration, using techniques as set forth in published US Patent Application No. 2003 0022833 (Wagner et al.). The concentration of hPRL-BP following ultrafiltration may be determined by protein assay and confirmed by Western Blot analysis using anti-His antibody (Santa Cruse, Calif.) and may be quantified by densitometry methods (Fernadez and Kopchick, Anal. Biochem. 191:268-271 (1990)).

Alternatively, a truncated PRL-BP may be made by protein synthesis techniques, e.g., by use of a peptide synthesizer. In addition, truncated PRL-BP may be prepared by purification of full length PRLR protein, from either naturally occurring or genetically engineered PRLR producing cells, followed by enzymatic cleavage of the purified protein using proteolytic enzymes, such as trypsin, to form PRL-BP.

The present invention also provides a cell-based assay system that can be used to identify compounds or compositions that modulate PRLR activity, and therefore, may be useful in combination therapy for regulation of cell proliferation and treatment of diseases associated with aberrant cell proliferation. In other words, any compound that interferes with prolactin signaling such that phosphorylation of HER2 is inhibited, is suitable for use in combination therapy with an agent that inactivates the HER2/neu signaling pathway. An exemplary agent that inactivates the HER2/neu signaling pathway is one that blocks HER2/neu, such as HERCEPTIN® (trastuzamab). The cell-based assay system of the invention is designed to assay for tyrosine phosphorylation. The assay system is based on the observation that the PRLR antagonist G129R is surprisingly capable of synergistically inhibiting breast cancer cell proliferation in combination with HERCEPTIN® (trastuzamab).

The present invention also provides a method for identifying a compound capable of modulating prolactin receptor activity, comprises the following steps:

a. contacting a compound to a cell that expresses the prolactin receptor;

b. measuring the level of apoptosis in the cell; and c. comparing the level of apoptosis obtained in (b) to the level obtained in the absence of the compound;

such that if the level obtained in (b) differs from that obtained in the absence of a compound, a compound capable of modulating prolactin receptor activity has been identified. If the level of apoptosis is increased in such an assay an antagonist of the prolactin receptor has been identified. Such identified prolactin receptor antagonists can be used in combination therapy with an agent that inactivates the HER2/neu signaling pathway. An exemplary agent that inactivates the HER2/neu signaling pathway is one that blocks HER2/neu, such as HERCEPTIN® (trastuzamab).

In yet another embodiment of the invention, a method for identifying a compound capable of inducing the activity of the prolactin receptor is provided that comprises the following steps:

a. contacting a compound to a cell that expresses the prolactin receptor, in the presence and absence of a compound that induces prolactin receptor mediated apoptosis;

b. measuring the level of apoptosis in the cell in the presence and absence of the compound that induces prolactin receptor mediated apoptosis; and c. comparing the levels of apoptosis obtained in (b));

such that if the level of apoptosis is decreased in the presence of the compound that induces prolactin receptor mediated apoptosis, a compound capable of activating the activity of the prolactin receptor has been identified.

To this end, cells that endogenously express PRLR can be used to screen for compounds that modulate the activity of the receptor. In a preferred embodiment of the invention the cells are transformed cells, such as for example, breast cancer cells or prostate cancer cells. In addition, cells that do not normally express PRLR can be genetically engineered to express the PRLR gene and such cells may be used for screening purposes. Those of skill in the art recognize that any cell line capable of transfection, and having low to no background level of the PRLR is acceptable.

In utilizing such cell-based assay systems, the cells expressing PRLR are exposed to a test compound or to vehicle controls (e.g., placebos). In assays designed for identification of PRLR agonists, compounds that induce PRLR mediated apoptosis, such as G129R, are also added to the assay. After exposure, the cells can be assayed to measure for the level of apoptosis. Assays designed to measure apoptosis include the terminal deoxynucleotidyl transferase mediated dUTP nick end labeling (TUNEL) assay (Kebers et al., *Experimental Cell Research* 240:197-205 (1998)); assays to detect activated caspases (Janicke et al., *J. Biol. Chem.*, 273: 9357-9360 (1998)); DNA ladder gel assays to detect fragmented DNA by gel electrophoresis (Bursch et al., *Carcinogenesis* 17:1595-1607 (1996)); assays to detect bcl-2 and bax protein levels (Wuerzberger et al., *Cancer Res.*, 58:1876-1885 (1998)); Hoechst/DAPI staining to detect nuclear condensation in apoptotic cells (Bursch et al., *Carcinogenesis*, 17:1595-1607 (1998)); Annexin V staining of phosphatidyl serine on the cytoplasmic membrane (van Engeland et al., *Cytometry*, 24:131-139 (1996)); analysis of DNA content by propidium iodide staining followed by flow cytometry (Sherwood et al., *Methods in Cell Biol.*, 46:77-97; and morphological studies using electron and phase contrast microscopy (Bursch et al., *Carcinogenesis*, 17:1595-1607).

The ability of a test compound to induce the level of apoptosis, above those levels seen with cells treated with a vehicle control, indicates that the test compound acts as an antagonist to inhibit signal transduction mediated by PRLR. Such compounds are suitable for use in combination therapy with HERCEPTIN® (trastuzamab). In contrast, the ability of a test compound to reduce the level of apoptosis in the presence of compounds such as G129R, above those levels seen with cells treated with a vehicle control, indicates that the test compound induces signal transduction mediated by PRLR.

High throughput screening can be accomplished by plating the test cells into wells of microtiter plates, each of which will contain a potential PRLR antagonist or agonist. The wells will also contain complete medium, and in instances where an agonist is to be identified, a compound such as G129R is included. After incubation with potential antagonists or agonists, the cells are assayed for apoptosis using methods such as those described above. Potential antagonists are those compounds that induce apoptosis in cells expressing the PRLR. Potential agonists are those compounds that compete with G129R for receptor binding and thereby inhibit G129R induced apoptosis.

The compounds which may be screened in accordance with the invention include, but are not limited to inorganic compounds, peptides, antibodies and fragments thereof, and other organic compounds (peptidomimetics) that bind to PRLR and either activate the activity of PRLR (i.e., agonists) or inhibit the activity of PRLR (i.e., antagonists). Compounds may include, but are not limited to, peptides such as, for example, soluble peptides, including but not limited to members of random peptide libraries; (see, e.g., Lam et al., *Nature* 354:82-84 (1991); Houghten et al., *Nature* 354:84-86 (1991)), and combinatorial chemistry-derived molecular library made of D- and/or L-configuration amino acids, phosphopeptides (including, but not limited to, members of random or partially degenerate directed phosphopeptide libraries; see, e.g., Songyang et. al., *Cell,* 72:767-778 (1993)). Screening the libraries can be accomplished by any of a variety of commonly known methods. In a specific embodiment of the invention, peptide variants of PRL may be screened for their ability to regulate the activity of the PRLR.

Compounds identified via assays such as those described herein may be useful, for example, for ameliorating diseases associated with aberrant cell proliferation. Assays for testing the efficacy of compounds identified in the screens can be tested in animal model systems for proliferative disorders, such as cancer.

Compositions and Methods

The present invention provides for methods and compositions whereby a PRL variant or a truncated form of the PRLR (which competes with endogenous receptor for PRL binding) may be used to inhibit the effects of PRL, and in particular, may be used to inhibit PRL-mediated cell proliferation. The method of the invention comprises administering an agent that inactivates the HER2/neu signaling pathway, such as HERCEPTIN® (trastuzamab), and either a prolactin variant, or a truncated form of the PRLR, to a subject having a proliferative condition wherein the proliferating cells express a prolactin receptor.

In particular specific nonlimiting embodiments, a PRL variant or a truncated PRLR (also referred to as a PRL-BP) of the invention may be tested for the ability to antagonize PRL activity in a panel of cell lines expressing different levels of the PRLR and/or PRL, so as to permit the inference of an effect which varies according to PRL/PRLR availability. For example, the activity of a hPRL variant or a truncated hPRLR may be tested in all or a subset of the following five different human breast cancer cell lines (T-47D, MCF-7, HTB19, HTB20, and HTB123 from ATCC). The hPRL receptor numbers on these cell lines have been reported to be: T-47D (25,800/cell), MCF-7 (8,300/cell), HTB19 (6,435/cell), HTB20 (5,480/cell), HTB123 (1,094/cell, normal breast cell=1,700/cell). Therefore, these cell lines represent a spectrum of hPRL receptor levels on human breast cancer cells. It should be noted that the use of human breast cancer cell lines is preferred over the use of the rat Nb2 T-cell lymphoma cell line, widely used in the lactogenic hormone studies, in order to avoid the potential confusing effects caused by species specificity.

Assays which may be used to determine the effects of the PRL variant or the truncated PRLR, either alone or in combination with HERCEPTIN® (trastuzamab) include (i) (for variant PRL) a competitive receptor binding assay, to examine if the antagonists are competing at the receptor level; (ii) detection/quantitation of phosphorylation of STAT 5, MAPK, or Akt protein to examine if the combination or putative antagonist inhibits the intracellular signal transduction induced by PRL; and (iii) a cell proliferation assay, which is used as an overall test for the potential inhibitory effects of the variant PRL, the truncated PRLR or the combination therapy with an agent that inactivates the HER2/neu signaling pathway. An exemplary agent that inactivates the HER2/neu signaling pathway is one that blocks HER2/neu, such as HERCEPTIN® (trastuzamab).

Conditions which may benefit from the administration of a PRL variant or a PRL-BP, in combination with an agent that inactivates the HER2/neu signaling pathway, include both benign and malignant proliferation of cells which express a PRLR or HER2/neu protein. Such conditions include but are not limited to proliferative diseases of the breast, including benign conditions such as breast adenomas and fibrocystic disease, and malignant conditions such as breast cancer, including ductal, cirrhosis, medullary, colloid and lobular carcinomas (local or metastatic); and proliferative diseases of the prostate, including benign prostatic hypertrophy and prostate cancer (local or metastatic). Proliferative conditions involving cells which express a receptor homologous to the PRLR may also be treated, including conditions involving cells which express a growth hormone receptor.

As set forth in published US Patent Application No. 2003 0022833 (Wagner et al.), prolactin variants/prolactin receptor antagonists are capable of inducing cellular apoptosis in human breast cancer cells and prostate cancer cells. Thus, the present invention provides methods for inducing apoptosis in cells expressing the prolactin receptor, as well as cells expressing a receptor homologous to the prolactin receptor, thereby inhibiting proliferation of such cells. In an embodiment of the invention, expression of the PRLR receptor can be targeted to a specific cell population targeted for apoptosis, such as a cancer cell population. Nucleic acid molecules expressing PRLR can be transferred into the targeted cell population using methods such as those employed in gene therapy protocols. Once expressed on the surface of the targeted cell population, the receptor can be activated through contact with prolactin variants to induce apoptosis of the targeted cell.

In the treatment of proliferative conditions, the PRL variant or PRL-BP may be administered either in a sequential or combined treatment regimen with an agent that blocks the HER2/neu signaling pathway. As nonlimiting examples, where the condition to be treated is breast cancer, additional agents used in a combined regimen may include an agent that inactivates the HER2/neu signaling pathway. The agent that inactivates the HER2/neu signaling pathway may be an agent that blocks HER2/neu. In some embodiments, the agent that blocks HER2/neu is a humanized monoclonal antibody, such as HERCEPTIN® (trastuzamab). For example, HERCEPTIN® (trastuzamab) may be administered concurrently or sequentially with a prolactin variant such as G129R. Where the condition to be treated is prostate cancer, additional agents used in a combination regimen may also be included, such as an anti-androgen and/or a chemotherapeutic agent. A combined treatment regimen is based on the observation that the use of a prolactin variant, in combination with a humanized monoclonal antibody such as HERCEPTIN® (trastuzamab), exhibited a synergistic inhibitory effect.

The present invention accordingly provides for compositions comprising an agent that inactivates the HER2/neu signaling pathway and a PRL variant or PRL-BP, in a suitable pharmaceutical carrier, for use in the foregoing methods. For therapeutic applications, the compositions of the present invention are administered to a mammal, preferably a human, in a pharmaceutically acceptable dosage form, including those that may be administered intravenously as a bolus or by continuous infusion over a period of time, by intramuscular, intraperitoneal, intracerebrospinal, subcutaneous, intra-arterial, intrasynovial, intrathecal, oral, topical, or inhalation routes. The compositions of the present invention are also suitably administered by intratumoral, peritumoral, intralesional or perilesional routes, to exert local as well as systemic effects. The intraperitoneal route is expected to be particularly useful, for example, in the treatment of various cancers and metastatic lesions.

The compositions of the present invention can be formulated according to known methods to prepare pharmaceutically useful compositions, whereby the agents of the composition are combined in an admixture with a pharmaceutically acceptable carrier vehicle. Suitable vehicles and their formulation, inclusive of other human proteins, e.g., human serum albumin, are described, for example, in REMINGTON'S PHARMACEUTICAL SCIENCES (16th ed., Osol, A., ed., Mack, Easton Pa. (1980)). To form a pharmaceutically acceptable composition suitable for effective administration, such compositions will contain an effective amount of one or more of the proteins of the present invention, together with a suitable amount of carrier vehicle. For example, the pharmaceutical compositions suitable for use in the present invention include compositions containing an agent that inactivates the HER2/neu signaling pathway and a PRL variant or PRL-BP in an effective amount to achieve its intended purpose. More specifically, an effective dose refers to that amount of HERCEPTIN® (trastuzamab) and a PRL variant or PRL-BP required to inhibit proliferation of cells expressing the PRLR thereby decreasing the symptoms associated with a proliferative condition. Determination of effective amounts is well within the capability of those skilled in the art.

The compositions for use in accordance with the present invention may be formulated in conventional manner using one or more physiologically acceptable carriers or excipients. Thus, they may be formulated for administration by inhalation or insufflation (either through the mouth or the nose) or oral, buccal, parenteral or rectal administration.

For oral administration, the pharmaceutical compositions may take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound. For buccal administration the composition may take the form of tablets or lozenges formulated in conventional manner.

For administration by inhalation, the compositions according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g. gelatin for use in an inhaler or insufflator may be formulated containing a powder mix of the compound and a suitable powder base such as lactose or starch.

The compositions of the present invention may be formulated for parenteral administration by injection, e.g., by bolus injection or continuous infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The composition may also be formulated in rectal compositions such as suppositories or retention enemas, e.g., containing conventional suppository bases such as cocoa butter or other glycerides.

In addition to the formulations described previously, the compositions of the present invention may also be formulated as a depot preparation. Such long acting formulations may be administered by implantation (for example subcutaneously or intramuscularly) or by intramuscular injection. Thus, for example, the prolactin variant and/or agent that inactivates the HER2/neu signaling pathway may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

Furthermore, the compositions of the present invention can also be modified to have a longer clearance rate and therefore increase bioavailability by protecting the composition from an immune response and other clearance mechanisms afforded by the subject. Indeed, WO 9/2802 discloses that PEGylated compounds exhibit reduced immunogenicity and antigenicity, and circulate in the bloodstream considerably longer than unconjugated proteins. For example, PEG (polyethylene glycol) polymer chains can be attached to the prolactin variant/prolactin receptor antagonist by methods known in the art, such as by the PEGylation procedure described in Roberts et al., *Adv. Drug Del. Rev.*, 54(4):459-76 (2002). But other agents which can prolong elimination half-life of the therapeutic composition of the present invention are known to the skilled artisan and contemplated herein.

In fact, the compositions described herein can also be modified with hydroxyethylstarch (HES). HES is a derivative of naturally occurring amylopektine and is degraded by α-amylase in the body. Methods for making HES-protein conjugates are known in the art. See, for example, EP 1398322, DE 2616086 and DE 2646854, which are incorporated herein by reference.

Agents that link the prolactin receptor antagonist to serum albumin are also contemplated in the present invention to prolong clearance time and increase half-life of the inventive composition. While such agents are disclosed in WO 01/45746, which is incorporated herein by reference, other peptide ligands which have an affinity for serum albumin that can be conjugated to the prolactin receptor antagonist of the present invention are also considered suitable for use herein.

The effective concentrations of the compounds of the invention may be established in cell culture systems and/or in transgenic animals. The effective dose may be determined using a variety of different assays. For example, cell proliferation assays may be conducted to quantitate the concentration of an agent that inactivates the HER2/neu signaling pathway and PRL variant or PRL-BP required to inhibit cell proliferation. Likewise, the concentration of PRL variant or PRL-BP to inhibit MAPK, JAK/STAT, or Akt activity can be readily performed using assays that measure phosphorylation. In addition, assays may be performed to quantitate the concentration of an agent that inactivates the HER2/neu signaling pathway and PRL variant or PRL-BP required to induce cellular apoptosis. Inhibition of tumor cell growth can be assayed to detect PRL variant or PRL-BP mediated inhibition of tumor cell proliferation. In such instances, the effective dose of PRL variant, PRL-BP, or agent that inactivates the HER2/neu signaling pathway is that amount required to decrease the proliferation of cancer cells, induce apoptosis, or slow the growth of a tumor in a patient. Determination of effective amounts of these compounds is well within the capability of those skilled in the art.

The amount of the composition will, of course, also be dependent on the subject being treated, the proliferative disorder being treated, the severity of the disorder symptoms and the judgment of the prescribing physician. In some instances it may be necessary to adjust the treatment to a lower dose due to undesirable side effects as well as adjusting the treatment to higher levels if the clinical response is not adequate.

Determining a therapeutically effective amount specifically will depend on such factors as toxicity and efficacy of the medicament. Toxicity may be determined using methods well known in the art and found in the foregoing references. Efficacy may be determined utilizing the same guidance in conjunction with the methods described below in the Examples. A pharmaceutically effective amount, therefore, is an amount that is deemed by the clinician to be toxicologically tolerable, yet efficacious. Efficacy, for example, can be measured by the decrease in mass of the targeted tissue. One of skill in the art would know what dosage is suitable for treatment based on consideration of these factors.

The invention is further described by reference to the following examples, which are provided for illustration only. The invention is not limited to the examples but rather includes all variations that are evident from the teachings provided herein.

Example 1

Design of a Prolactin Receptor Antagonist

Since there is no crystal structural data presently available regarding hPRL, a computer algorithm program developed by Garnier et al., *J. Mol. Biol.*, 120:97-120 (1978), was used to analyze and compare the secondary structures of hPRL and hGH. The results showed that the overall alpha-helix regions are very similar, suggesting that these hormones share a similar overall conformation. When the amino acid sequences in the third alpha-helix were compared between GHs and PRLs, it is clear that the Gly 129 of hPRL corresponds to Gly 120 of hGH and it is absolutely conserved among the GH/PRL family (Chen et al., *J. Biol. Chem.* 269:15892-15897 (1994)). Therefore, a Gly to Arg substitution mutation in hPRL was prepared in order to generate a hPRL receptor specific antagonist.

Example 2

Preparation of G129R

Cloning of the Human Prolactin Gene

Human PRL was successfully cloned using reverse transcription (RT) followed by polymerase chain reaction (PCR). Briefly, human pituitary polyA RNA (CloneTech, Inc. Palo Alto, Calif.) was used as template. A hPRL antisense primer was designed starting 2 bases from the stop codon (TAA) of hPRL cDNA (5' GCTTAGCAGTTGTTGTTGTG 3' SEQ ID NO:1) and a sense primer was designed from ATG (5' ATGAACATCAAAGGAT 3' SEQ ID NO:2). RT/PCR was carried out using a kit from Perkin-Elmer Cetus, Inc. (Norwalk, Conn.). The nucleotide sequence of the resulting hPRL was determined by the dideoxy chain-termination method using modified T7 DNA polymerase (Sequenase, United States Biochemical), and was found to be identical to that reported in GenBank except for a one base difference which results in a silent mutation at codon 21 (CTG→CTC). A schematic representation of the cloning process, including preparation of the pUCIG-Met expression vector, is summarized in published US Patent Application No. 2003 0022833 (Wagner et al.), which is incorporated herein by reference in its entirety.

Creation of the G129R Prolactin Variant

The parental plasmid which contains the hPRL cDNA and a M13 F1 origin of replication was transformed into *E. coli* (CJ236). Single stranded plasmid DNA containing uridine was isolated from the transformed CJ236 bacteria using the helper bacteriophage, M13k07. Six pmol of oligonucleotide containing sequence directing the G129R mutation was annealed with 0.2 μmol of single stranded DNA in annealing buffer (200 mM Tris-HCl, 20 mM MgCl$_2$, 100 mM NaCl) by heating to 70° C. for 5 minutes followed by slow cooling. The oligonucleotide (5'CGGCTCCTAGAGAGGATG-GAGCT3' SEQ ID NO. 3), which encodes the G129R mutation was used to prime synthesis of a complementary strand of DNA, using single stranded DNA as a template, that is catalyzed by T4 DNA polymerase. After synthesis, the double stranded DNA was used to transform *E. coli* (DH5a). Individual clones were isolated and screened for hPRL-G129R by DNA nucleotide sequencing. The G129R hPRL variant is hereafter referred to as hPRLA, the "A" referring to its antagonist activity.

Expression of Cloned Proteins

The hPRL and hPRLA-encoding nucleic acids were each inserted into a mammalian cell expression vector in which transcription of the cDNAs is controlled by the mouse metallothionein enhancer/promoter sequence and bGH poly A addition signal (Chen et al., *J. Biol. Chem.*, 266:2252-2258 (1991); Chen et al., Endocrinol., 129:1402-1408 (1991); Chen et al., Mol. Endocrinol., 5:1845-1852 (1991); Chen et al., J. Biol. Chem., 269:15892-15897 (1994)). To establish stable mouse L cell lines which produce hPRL and hPRLA, mouse L cells [thymidine kinase-negative (TK) and adenine phosphoribosyl transferase-negative (APRT)] were selected as an in vitro expression system. Stable cell lines which express HPRL (which will be used as positive control) and hPRLA (~5-10 mg/1/24 h/million cells) were prepared.

Membrane ultrafiltration was used to partially purify as well as concentrate hPRL and hPRLA from conditioned cell culture media, using techniques as set forth in Chen et al., *J. Biol. Chem.* 269:15892-15897 (1994). The separation is based on the relative molecular size and the pore size of membrane. The ultrafiltration membranes were obtained from Amicon, Inc. (Northorough, Mass.). Two types of membranes were used, YM10 and YM100. A 200 ml stirred cell with Amicon YM100 under 20 psia transmembrane pressure was first used for removal of large impurities from the culture media. The permeate (>90% of recovery of hPRL) was applied onto a second filtration protocol which uses YM10 membrane to reduce the volume of solution and thus concentrate the protein. The concentration of HPRL or hPRLA was determined using an immunoradiometric assay (IRMA) kit from Diagnostic Products Corp. (Los Angeles, Calif.).

Example 3

Inhibitory Activity of G129R

Materials and Methods

Radioreceptor binding assay. Purified I:PRL was labeled with Na $^{125}$I by the lactoperoxidase method to a specific activity of 80-105.mu.Ci/.mu.g as described in Harding et al., 1996, J. Biol. Chem. 271:6708-6712. Briefly, 1.0 mCi of Na$^{125}$I was added to 1 mg of HPRL. Lactoperoxidase (10 μg dissolved in 10 μl of 0.4 mol/liter acetate butter, pH 5.6) and H$_2$O$_2$ (5 μl of 1.76 mmol/liter) were then added. After 30 min, the reaction was terminated by the addition of 100 μl of transfer buffer (0.47 mol/liter sucrose, 0.06 mol/liter KI, sodium azide 0.02%, pH 7.6). Radiolabeled hPRL was then separated by SEPHADEX® (cross-linked dextran gel) G-100 chromatography. Human breast cancer cells were plated in 6-well plates. After preincubation in serum-free DMEM for 2-3 hours to deplete serum, the monolayer of cells was exposed to serum-free conditioned medium containing $^{125}$I-hpRL (50,000 cpm) in the presence of various concentration of HPRL or hPRLA for 2-3 hours at 37° C. After incubation at room temperature for 3 hours, the cells were washed with phosphate-buffered saline (PBS) two times, and then lysed in 1 ml of 1% SDS/0.1N NaOH. The CPM in lysates were then determined Non-specific binding was measured by adding 5 ng/ml of unlabeled hPRL in regular mouse L cell conditioned media to control nonspecific displacement.

Assay of hPRL induction of tyrosine phosphorylation of STAT5 protein. STAT proteins represent a family of proteins, having molecular masses of approximately 92-95 kDa, which have been found to be tyrosyl phosphorylated when GHR or PRLR containing cells are treated with GH or PRL, respectively. Tyrosyl phosphorylation of STAT 5 is a receptor mediated event and is thought to be an important step in ligand-induced signal transduction (Wakao et al., *EMBO J.*, 13:2182-2191 (1994); Kazansky et al., *Mol. Endocrinol.*, 9:1598-1609 (1995); Waxman et al., *J. Biol. Chem.*, 270: 13262-13270 (1995)). This assay was used to evaluate the ability of hPRL and hPRLA to inhibit induction of STAT 5 phosphorylation by wild type PRL.

Briefly, human breast cancer cells were plated in 12-well plates. After pre-incubation in serum-free DMEM for 2-3 hours, the cells were exposed to various concentration of hPRL and hPRLA in serum-free DMEM. The cells were incubated for 15 mM at 37° C., washed once with PBS, and lysed in 300 μl lysis buffer (50 mM Tris-HCl, pH 6.8, 1% SDS, 1% (3-mecaptoethanol, 0.1M DTT, 5% Sucrose, 100 uM Sodium Orthovanadate, and 0.6% bromphenol blue). Thirty microliters of cell lysates were subjected to 4-12.5% SDS-PAGE and immunoblot analysis using horse radish peroxidase (HRP)-conjugated anti-phosphotyrosine antibody PY20 and ECL reagent kit (Amersham, Ill.). Blots were then exposed to X-ray films and developed using standard procedures (Kodak, Rochester, N.Y.). This assay has been described in Chen et al., J. Biol. Chem., 269: 15892-15897 (1994); Chen et al., Endocrinol., 136:660-667 (1995); Wang et al., Proc. Natl. Acad. Sci. U.S.A., 91:1391-1395 (1994); Chen et al., Mol. Endocrinol., 9(3):292-302 (1995); Harding et al., J. Biol. Chem., 271(12):6708-6712 (1996).

Cell proliferation assays. hPRLA was tested for its ability to inhibit breast cancer cell proliferation in tissue culture. The human breast cancer cells were grown in corresponding culture media according to ATCC recommendations. Cells were maintained at 37° C. in a humidified atmosphere of 5% CO$_2$ in air. The assay conditions were essentially as described by Ginsburg and Vonderharr (*Cancer Res.*, 55:2591-2595 (1995)). For individual growth experiments, cells were plated in 12 well culture plates at a density of approximately 2×10$^4$/ml, 1 ml/well. Cells were then allowed to attach for one day (T-47D, MCF-7, HTB19, and HTB20 cells, except for HTB 123, which is a suspension cells), then the overlying media was removed and changed to serum-free conditions with media containing ITS (insulin-transferring-selenium-BSA-linoleic acid culture supplement; Collaborative Research Bedford, Mass.). Varying concentrations of hPRL alone or in combination with hPRLA were introduced. After an additional three days in culture, cells were harvested after brief trypsinization and counted in a cell counter.

For certain experiments, a mixed cell culture assay was used. In this assay, breast cancer cells were co-cultured with expressor cells which had been transfected with nucleic acid encoding PRL or a PRL variant and expressing those recombinant proteins. By varying the number of expressor cells, the amount of PRL or PRL variant present in the mixed cell culture was increased or decreased. A fixed number of breast cancer cells (T47D) were added to wells of a multi-well cell culture plate. In certain wells, which served as a control, no expresser cells were added. Then, increasing numbers of expresser cells (transfected L cells expressing either HPRL (L-PRL) or hPRLA (L-PRLA)) were added to breast cancer cell-containing wells to create mixed cultures. The same numbers of expresser cells were cultured in parallel (without T47D cells) to serve as controls. After culturing under standard conditions for a period of time, the number of cells present in the wells was counted, and the number of L cells in the corresponding control culture was subtracted. The resulting number could then be compared to the number of T47D cells in the T47D control culture to evaluate the effects of the recombinant product on breast cancer cell proliferation.

Results and Discussion

Results of radioreceptor binding assay. The results of the assay performed using T-47D and HTB 123 cells along with a panel of human cancer cells. They demonstrated that two cell lines (T-47D and HTB 123) among those tested contain minimum hGH receptor specific binding as compared to human leukemia cells, lymphoma cells and retinoblastoma cells.

Phosphorylation of STAT5 proteins. Experiments testing the abilities of hPRL and hPRLA, and combinations thereof, to induce phosphorylation of STAT5 proteins in T-47D human breast cancer cells have demonstrated that hPRLA is able to block the signal transduction induced by hPRL, thereby demonstrating the antagonistic activity of PRLA.

Cell Proliferation Assays.

Cell proliferation assay results from experiments in which T-47D cells were exposed to either hGH or hPRL indicate that similar mechanisms (i.e., one ligand leading to dimerization of receptors) are used by both GH and PRL signal transduction. Since the affinity of binding site one of the ligand is apparently much higher than the affinity at binding site two, at high concentrations of hormone, all receptors are occupied by a single ligand via the high affinity site (the "self-antagonism's phenomenon").

In a study comparing the effects of HPRL and G129R to the effects of estrogen and the estrogen antagonist tamoxifen, results indicate that HPRL and estrogen increased proliferation of T47D cells (relative to untreated control cultures) and hPRLA and tamoxifen had a comparable inhibitory effect.

Example 4

Cloning of the Prolactin Receptor hPRL-BP cDNA was cloned using reverse transcription (RT) followed by the polymerase chain reaction (PCR). The hPRL-BP antisense primer was designed at a NcoI restriction enzyme cutting site which is located 66 bases from the putative transmembrane domain and a stop codon (TGA) was incorporated (5'GCACTTCAGTATCCATGGTCTGGT 3' SEQ ID NO: 4). The sense primer was designed including translational start codon ATG (5' AGAAGGCAGCCAAC {fraction (ATG)}AAG 3' (SEQ ID NO: 5). RT/PCR was carried out by using a kit from Perkin-Elmer Cetus, Inc. (Norwalk, Conn.). The nucleotide sequence hPRL-BP was determined by the dideoxy chain-termination method using modified T7 DNA polymerase (Sequenase, United States Biochemical).

Example 5

Human Prolactin Receptor Antagonist G129R Induced Apoptosis in Multiple Human Breast Cancer Cell Lines and Prostate Cancer Cells Materials and Methods
Cell Lines.

The human breast cancer cell lines MDA-MB-134, T-47D, BT-474 and MCF-7 were obtained from ATCC. These breast cancer cell lines were chosen based on their PRLR levels. The cell line T-47D had the highest PRLR level followed by MDA-MB-134, BT-474, MCF-7 in decreasing order of PRLR levels (Peirce S and Chen W Y., 2001, J. Endocrinol. 171:R1-4).

Cell Culture.

T-47D cells obtained from ATCC were grown in RPMI 1640 (phenol red free), supplemented with 10% FBS (GIBCO BRL). BT-474 cells were grown in RPMI 1640 medium (phenol red free) supplemented with 10% FBS and ATCC recommended supplements. MCF-7 cells were grown in DMEM medium (phenol red free), supplemented with 10% FBS. The cells were grown at 37° C. in a humid atmosphere in the presence of 5% $CO_2$. The MDA-MB-134 cells were grown in Leibovitz's L-15 medium supplemented with 20% FBS and grown in $CO_2$ free atmosphere. The breast cancer cells were trypsinized (0.02% Trypsin—EDTA) and grown in their respective media (phenol red free) supplemented with 10% CSS (Charcoal stripped serum) for a week. Subsequently the cells were trypsinized again and plated onto an 8 chambered slide system (Lab Tek II) at a confluence of 60-70% per chamber. The next day treatments were performed on the breast cancer cells using their respective media (phenol red free), supplemented with 1% CSS. The MDA-MB-134 VI cells were grown in phenol red containing medium, but with the same serum conditions as the other breast cancer cells.

Terminal deoxynucleotidyl transferase mediated dUTP nick end labeling (TUNEL) assay. Nicks of the fragmented DNA are labeled at their 3-OH ends. The fluorescein-labeled dUTP is incorporated at the 3-OH ends by using the enzyme terminal deoxynucleotidyl transferase. After the assigned period of treatment the chambers were dismantled as per the manufacturer's instructions and the TUNEL assay (Apoptosis detection system, Fluorescein-Promega) was performed as per the manufacturer's instructions. The slide was examined under a FITC filter using an Olympus IX 70 microscope system.

Results

Apoptosis (programmed cell death) is one of the central physiological mechanisms that regulates the timely and orderly death of cells (Stellar, H., 1995, Science 267:1445). The biochemical hallmark of apoptosis is internucleosomal DNA cleavage (Wyllu, Nature, 284:555 (1980); Roy et al., *Exp. Cell Res.*, 200:416-424 (1992); Wyllu, *Int. Rev. Cytol.*, 68:251-306 (1980)) and it can be detected by the TUNEL assay or by conventional gel electrophoresis (Chen, *J. Cell. Biochem.*, 61:9-17 (1996)). Cancer is a disease in which the malignant cells have a decreased ability to undergo apoptosis in response to at least some physiological stimuli (Hoffman et al., *Oncogene*, 9:1807 (1994)). Drugs that can induce cancer cells to undergo apoptosis could prove to be effective in cancer therapy.

As demonstrated herein, the PRLR antagonist G129R was able to induce apoptosis as detected by DNA fragmentation in multiple human breast cancer cell lines. DNA fragmentation in breast cancer cells was apparent even after 2 hours of treatment by G129R at a concentration of 50 ng/ml. In previous studies it was shown that 4-OH-Tamoxifen synergistically inhibited the proliferation of breast cancer cells along with G129R. Therefore, 4-0H-Tamoxifen was included in this study to verify that 4-OH-Tamoxifen also induced apoptosis in breast cancer cells by DNA fragmentation. Surprisingly, 4-OH-Tamoxifen did not induce apoptosis in T-47D, MCF-7 or BT-474 cells at a concentration as high as 1 μM as assayed by the same protocol despite the fact that 4-OH-Tamoxifen was able to inhibit cell proliferation. In contrast to 4-OH-Tamoxifen, 250 ng of G129R induced apoptosis DNA fragmentation in all four PRLR positive breast cancer cell lines after 24 hours treatment.

In addition, the effect of hPRL-G129R on Caspase-3 activation was assayed in T-47D cells using an ApopAlert CPP32/Caspase-3 assay kit (Clontech, Palo Alto, Calif.). T-47D cells were treated with 250 ng/ml of hPRL-G129R for 2 h. The assay was performed in the presence of DEVD-CHO (caspase-3 inhibitor) to demonstrate that the Caspase-3 induction by hPRL-G129R is a specific event.

The data described above indicates that breast cancer cells are adapted to utilize prolactin as a major growth factor. Breast cancer cells undergo apoptosis when deprived of prolactin by competitively binding to G129R, leading to an inhibition of the PRL growth signal. Thus, the continued mitogenic signal provided by HPRL may override existing apoptotic signals within breast cancer cells permitting the delayed apoptosis process to proceed. The data presented herein indicates that the prolactin receptor antagonist G129R can be used in endocrine therapy in conjunction with tamoxifen, or by itself in the treatment of breast cancer.

In addition, two prostate cancer cells underwent apoptosis (as detected by TUNEL assay) in response to treatment with 250 ng hPRL-G129R for 24 hours. The samples were in duplicate and each sample constituted about 2 million cells.

Example 6

Co-Expression of PRLR and HER2 in Breast Cancer Cell Lines

Figure 2:
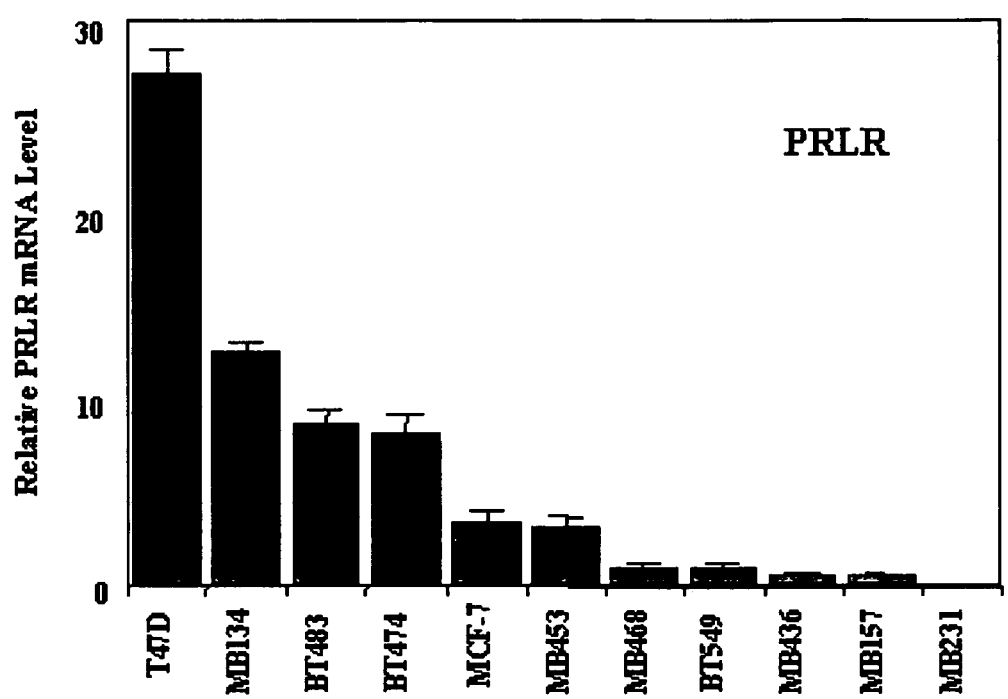
FIG. 2. Comparison of relative PRLR mRNA levels in eleven breast cancer cell lines and normal breast tissue, normalized to 100 ng of (3-actin RNA. Y-axis, fold difference.

The inventors conducted real time PCR assays to examine HER2 expression in 11 breast cancer cell lines (FIG. 1) and made a direct comparison with their relative hPRLR levels (FIG. 2). Based upon our preliminary results, six cell lines with high levels of hPRLR (T-47D, MDA-MB134, BT483, BT474, MCF-7 and MDA-MB453) also expressed high levels of HER2 compared to normal tissue. The highest HER2 overexpression was seen in the MDA-MB453 cell line (>100 fold over normal), which was also reported by others (Llovera, infra). On the other hand, five cell lines (MDA-MB468, BT549, MDA-MB436, MDA-MB157 and MDA-MB231) had relatively low hPRLR levels and relatively low HER2 levels (less than 5 fold higher than normal breast tissue). This suggests the close relationship between PRLR and HER2 systems.

Example 7

Figure 3:
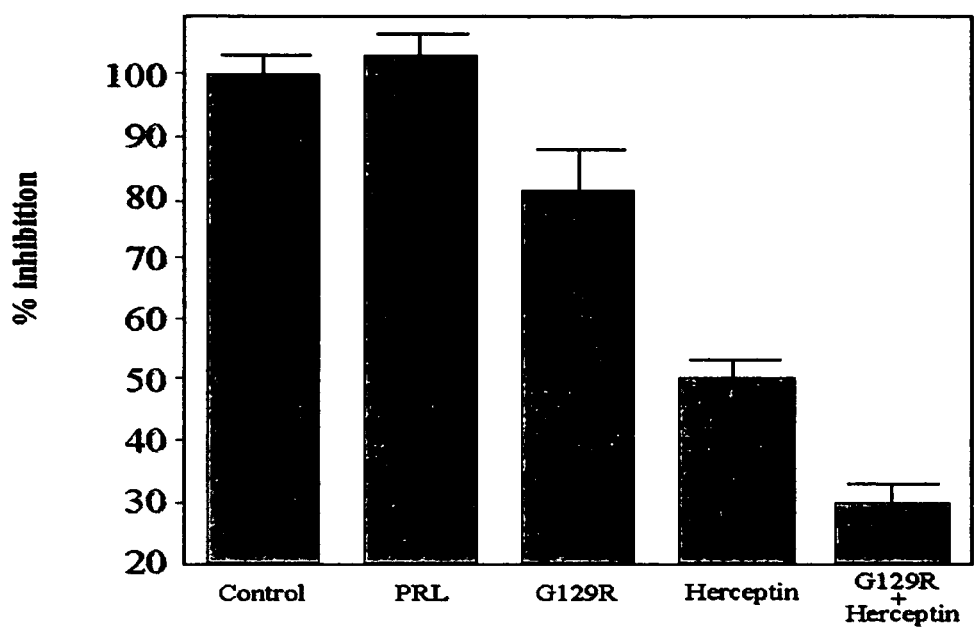
FIG. 3. Combination treatment of breast cancer cell lines with G129R and HERCEPTIN® (trastuzamab) inhibits cell proliferation. Cells were cultured (10,000 or 15,000 cells/well) in culture medium supplemented with hPRL (100 ng/ml), G129R (1 µg/ml), HERCEPTIN® (trastuzamab) (20 µg/ml) or G129R+HERCEPTIN® (trastuzamab) for 24 h. The y-axis represents percent viable cells after each treatment.

Synergistic Effect of HERCEPTIN® (Trastuzamab) and G129R in Inhibition of Breast Cancer-Cell Proliferation "In order to confirm the synergistic effects between G129R and HERCEPTIN® (trastuzamab), T-47D cells (highest levels of PRLRs) were used for preliminary studies with the ViaCount reagent and the Gauva PCA cytometer (Guava Technologies, Inc.). This assay permits the determination of the number of total and viable cells in cultures. Cell proliferation was determined as a measure of the number of viable cells after 24 hours of treatment (FIG. 3). Treatment with G129R results in a decrease in proliferative ability by 21.5% compared to untreated control cells whereas HERCEPTIN® (trastuzamab) treatment leads to a 54% decrease in cell number. As predicted, the combination treatment of T-47D cells with G129R and HERCEPTIN® (trastuzamab) had apparent synergistic effects on cell proliferation resulting in an 86.5% decrease in cell number.

Example 8

Figure 4:
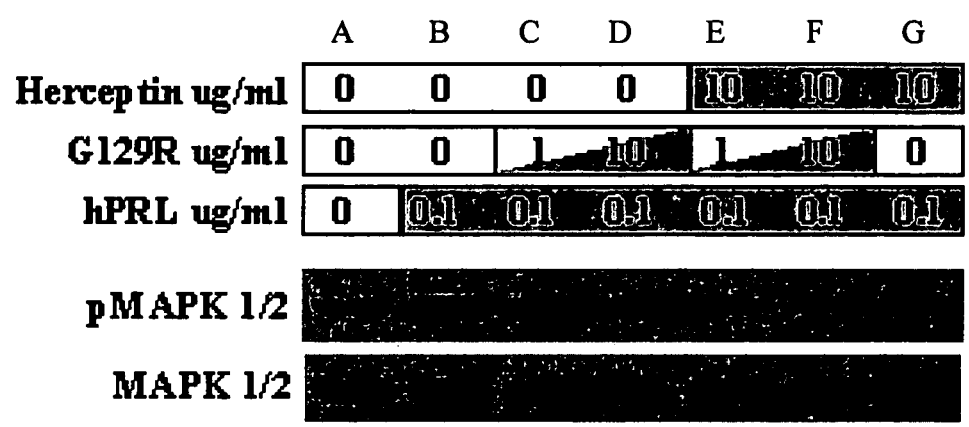
FIG. 4. Synergistic effects of G129R and HERCEPTIN® (trastuzamab) in inhibition of MAPK phosphorylation using T-47D human breast cancer cells. T-47D cells were cultured overnight in serum free media at 80% confluency and were treated for 30 minutes with hPRL (100 ng/ml, lane B to G) and in the presence of low or high doses of G129R (lanes C to F) without or with HERCEPTIN® (trastuzamab) (lanes C, D or E, F, respectively). Lane A, untreated cells as controls and lane G, HERCEPTIN® (trastuzamab) and PRL only. Membranes were stripped and re-probed with appropriate anti-MAPK antibody to ensure equal loading.
Figure 5:
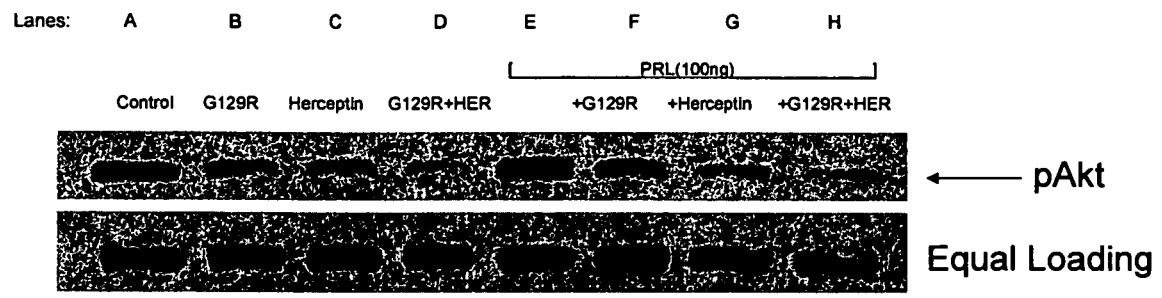
FIG. 5. Effect of HERCEPTIN® (trastuzamab) and G129R in inhibition of phosphorylation of Akt. T-47D cells were cultured overnight in serum free media at 60% confluency. Cells were treated for 48 hours with 10 µg G129R (Lane B), with 10 µg of HERCEPTIN® (trastuzamab) (Lane C), and with the combination of G129R and HERCEPTIN® (trastuzamab) (Lane D). Lane A is the control cells that are untreated. Cells were stimulated with hPRL (100 ng/ml, Lanes E to H) in the presence of G129R (Lane F), in the presence of HERCEPTIN® (trastuzamab) (Lane G), and in the combination of G129R and HERCEPTIN® (trastuzamab) (Lane H). Activation of Akt was analyzed by WB with anti-phospho-specific antibodies in 50 µg protein extracts. Lower panel shows the stripped membrane reprobed with the appropriate anti-Stat5 antibody to ensure equal loading.
Figure 6:
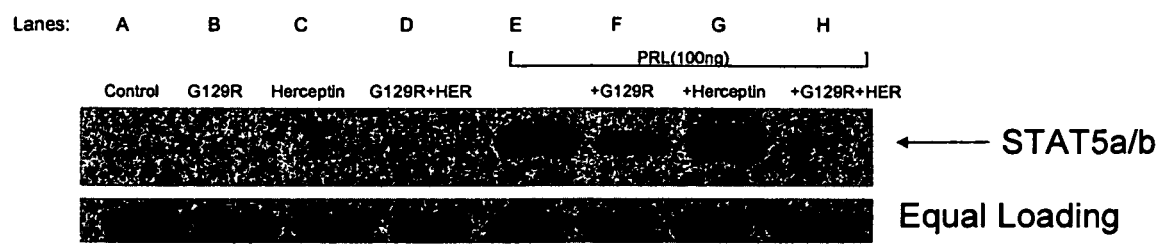
FIG. 6. Effect of HERCEPTIN® (trastuzamab) and G129R on inhibition of phosphorylation of Stat5a/b. T-47D cells were cultured overnight at 60% confluency and were maintained in phenol red-free and serum-free RPMI-1640 for 72 hours before stimulation. Cells were treated for 48 hours with 10 µg G129R (Lane B), with 10 µg of HERCEPTIN® (trastuzamab) (Lane C), and with the combination of G129R and HERCEPTIN® (trastuzamab) (Lane D). Lane A is the control cells that are untreated. Cells were also stimulated with hPRL (100 ng/ml, Lanes E to H) in the presence of G129R (Lane F), in the presence of HERCEPTIN® (trastuzamab) (Lane G), and in the combination of G129R and HERCEPTIN® (trastuzamab) (Lane H). Activation of Stat5 was analyzed by WB with anti-phospho-specific antibodies in 50 µg protein extracts. Lower panel shows the stripped membrane reprobed with the appropriate anti-Stat5 antibody to ensure equal loading. As Stat is a signaling molecule for PRL and not HER2, here the inhibitory effect of G129R is demonstrated in the presence of hPRL, but not HERCEPTIN® (trastuzamab). However an inhibitory effect of Stat phosphorylation is still apparent when treated with the combination of G129R and HERCEPTIN® (trastuzamab).

Synergistic Effect of HERCEPTIN® (Trastuzamab) and G129R in Inhibition of Phosphorylation of MAPK It has been demonstrated that hPRL treatment of T-47D cells induced p44 (MAPKI/Erk1) and p42 (MAPK2/Erk2) phosphorylation after 15-30 min of stimulation. This PRL induced activation of MAPK activity can be attenuated by the addition of G129R (Llovera et al., *Oncogene* 19:4695-705 (2000)). Since MAPK is also a signaling molecule for HER2, we tested the possibility of a synergistic inhibitory effect between G129R and HERCEPTIN® (trastuzamab). Our data demonstrated that there is indeed a synergistic effect between G129R and HERCEPTIN® (trastuzamab) (FIG. 4, lanes E and F).

Example 9

Cell Lines and Materials Used in Examples 10-12

Five human breast cancer cell lines are used in this study: Four cell lines (T-47D, MCF-7, BT-474, and MDA-MD-453) are chosen primarily because they co-express relatively high levels of hPRLR as well as HER2 (Peirce et al., *J. Endocrinol.*, 171:R1-4 (2001). In addition, one breast cancer cell line (MDA-MB435) is included in this study since it expresses very low levels of both PRLR and HER2/neu, thus serve as controls. HERCEPTIN® (trastuzamab) is purchased from Cancer Center of Greenville Hospital System. The G129R used in this study will be produced from *E. coli* according to our published protocols (Cataldo et al., *Stem Cells*, 17:138-146 (1999).

Example 10

Human Breast Cancer Cell Proliferation Assays to Test the Efficacy of the Potential Synergistic Effect of G129R and HERCEPTIN® (Trastuzamab)

The purpose of this experiment is to confirm our preliminary results that indicated a potential synergistic effect between G129R and HERCEPTIN® (trastuzamab) in inhibiting breast cancer cell proliferation. To validate the results, multiple human breast cancer cell lines with various levels of HER2 and PRLR are selected. One breast cancer cell line that expresses very low levels of both PRLR and HER2 is included as a control. Complete dose-response and time course experiments for G129R, HERCEPTIN® (trastuzamab) and a combination of the two drugs are conducted for each of the cell lines. The results of these experiments confirm the efficacy of G129R and HERCEPTIN® (trastuzamab) in inhibiting cancer cell growth and provide valuable information for designing drug dose for animal studies. The information derived from this part of study provides potential guidelines for future clinical trials.

Methods:

The assay conditions are modified from those described (Ginsburg et al., *Cancer Res.*, 55:2591-2595 (1995). Briefly, breast cancer cells are trypsinized and passed into 96 well plates in RPMI-1640 media containing 0.5% FBS treated with dextran-coated charcoal (DCC-FBS) in a volume of 100 W/well. The optimal cell number/well for each cell line will be pre-determined after titration of each cell line (for example, we have found that 15,000 cell/well are optimal for T-47D as well as for MCF-7 cells). The cells are allowed to settle and adhere overnight (12-18 hours) and subsequently various concentrations of either hPRL, G129R, HERCEPTIN® (trastuzamab) or combinations in a total volume of 40 W of culture media is added. Cells will be incubated for an additional 24 hr, 48 hr, 72 hr and 96 hr at 37° C. in a humidified 5% $CO_2$ incubator. After incubation, MTSPMS solution (Cell Titer 96 Aqueous kit, Promega Corp.) is added to each well, following the manufacturer's instructions. Plates will be read at 490 nm using a BIO-RAD benchmark microplate reader. The experiments are carried out in triplicate and repeated three to six times for each cell line. An alternative cell proliferation assay that has recently been used in our lab will serve as a backup method. The method is based upon the ViaCount reagent and the Gauva PCA™ cytometer (Guava Technologies, Inc.), which permits a quick and convenient determination of the number of total and viable cells in cultures.

These experiments show that G129R and HERCEPTIN® (trastuzamab) inhibit breast cancer cell proliferation in a synergistic manner.

Example 11

D-3 Validate the Cross-Talk Mechanism Between hPRL and HER2/neu

Human PRL signals via cell surface specific receptors that lead to JAK2/STAT/MAPK activation, which ultimately promotes cell proliferation. Phosphorylation of HER2 protein is a crucial step in the activation of its downstream signaling molecules such as Ras/MAPK cascade. The present study verifies that (1) hPRL is able to phosphorylate HER2 in multiple breast cancer cells; (2) G129R is able to specifically block HER2 phosphorylation; and (3) combination treatment of HERCEPTIN® (trastuzamab) and G129R has synergistic inhibitory effects on MAPK. We also hope to demonstrate that the phosphorylation status of MAPK in breast tissue can be used as a valid biomarker in future clinical study.

Methods:

Immunoprecipitation experiments confirm the role of hPRL and G129R in regulation of phosphorylation of HER2 in multiple breast cancer cell lines. A panel of breast cancer cell lines with different levels of hPRLR and HER2 are treated with different doses of PRL (from ng/ml to ug/ml to establish a dose response curve) and terminated at the various time points (from 15 min to 24 hr to establish response time course). The optimal stimulatory dose and the response time courses are determined for each cell lines. Anti-HER2 antibody is used to immunoprecipitate HER2 in cell lysates and anti-phospho-HER2 antibody is used (Western blot) to identify the level of phosphorylated Her2 in response to the treatment.

The Western blot method is used to measure the phosphorylation status of MAPK using antiphospho-MAPK antibodies after similar treatment to confirm potential synergistic effects between G129R and HERCEPTIN® (trastuzamab) in multiple cell lines.

Example 12

Synergistic Anti-Tumor Effects Between G129R and HERCEPTIN® (Trastuzamab) using Human Breast Cancer Xenografts in Nude Mice The nude mouse study is a direct extension of in vitro studies and is used to confirm the potential synergistic effects of inhibition of both PRLR and HER2 in vivo. The half-life for HERCEPTIN® (trastuzamab) has been reported in the range of 5-7 days when a 2-4 mg/kg dose is used. The half-life for G129R is in the range of 1-2 hrs after a single injection. We use high doses for both drugs to obtain strong anti-tumor responses.

Methods:

Cell Lines and Animals: Two human breast cancer cell lines, T-47D and BT-474 will be selected for nude mouse studies. T-47D has high levels of both PRLR and HER2 whereas BT-474 cells have lower levels of both receptors. Both T-47D and BT-474 cells have been demonstrated in our hands to form progressively growing tumors when injected into the mammary fat pads (MFPs) of nude mice. These two cell lines are used for primary xenograft growth assays in response to the treatments (single agents or combination, Table I). Eight to ten-week old female Nuj/nude mice (The Jackson Lab; Bar Harbor, Me.) are used. The animals are maintained in a sterile environment in compliance with NIH guidelines.

Inhibition of Primary Xenograft Growth Assay: In our previous studies, we have demonstrated that 100% of mice inoculated at the MFP with T-47D cells or BT-474 cells developed tumors. The response from these two human breast cancer xenografts after G129R, HERCEPTIN® (trastuzamab) or combination reveal valuable information based upon their different receptor status (T-47D vs. BT-474). The dose regimen is temporary (Table I). The final adjustment of dose especially the combination and frequency, will be made after we complete cell proliferation assays.

Briefly, cells are grown in RPMI-1640 or DMEM medium containing 10% FBS. The cells are maintained in a humidified atmosphere containing 5% $CO_2$ at 37° C., according to ATCC recommendation to 95-100% confluence. Adherent cells will be detached using Trypsin (0.25% 1 mM EDTA), counted, resuspended in Matrigel at a concentration of $1 \times 10^7$ cells/200 W Matrigel, and injected into the MFPs of Nuj/nude mice. The mice are implanted with slow-releasing E2 (17-16 estradiol) pellets, s.c. (0.72 mg/60 day, Innovative Research of America, Inc.) to enhance tumor growth (for T-47D cells only). Three days after tumor cell inoculation, the mice are randomized into control and experimental groups. Mice will be treated with different regimens for at least eight weeks (see Table I).

TABLE I

The Experiment Design of Nude Mouse Study

| | Group I | Group II | Group III | Group IV |
|---|---|---|---|---|
| Primary Tumor Growth (T-47D and BT-474) | Saline | HERCEPTIN ® (trastuzamab) (4 mg/kg/twice weekly) | G129R (4 mg/kg/day) | HERCEPTIN ® (trastuzamab) + G129R |

Data Collection and Statistical Analysis: Tumors are measured along two major axes with calipers once a week. Tumor volume is calculated as follows:

$V = 4/3 \pi R_1^2 R_2$ where $R_1$ is short radius, $R_2$ is long radius. The results are presented as means±SE. Multiple statistical comparisons are performed using Analysis of variance (ANOVA). Tumors are dissected at the end of experiments and weighed. Comparisons between treated and control mice, as a function of time, are performed using ANOVA. The survival time of experimental animals are compared in metastatic groups. Results indicate a synergistic inhibitory effect of G129R and HERCEPTIN® (trastuzamab) in these xenografts.

Additional embodiments are within the scope of the invention. For example, the invention is further illustrated by the following numbered embodiments:

1. A method for inhibiting cell proliferation comprising exposing a target cell to a prolactin receptor antagonist and an agent that inactivates the HER2/neu signaling pathway.

2. The method of embodiment 1, wherein the prolactin receptor antagonist comprises an amino acid substitution at position 129

3. The method of embodiment 1, wherein the agent that inactivates the HER2/neu signaling pathway is HERCEPTIN® (trastuzamab).

4. The method of embodiment 2 or 3, wherein the HERCEPTIN® (trastuzamab) is administered concurrently or sequentially with the prolactin receptor antagonist.

5. The method of embodiment 4, wherein the target cell is selected from the group consisting of a breast cancer cell that expresses a prolactin receptor and a prostate cancer cell that expresses a prolactin receptor.

6. The method of embodiment 2, wherein the amino acid at position 129 is substituted with arginine.

7. A method for inducing apoptosis in a cell comprising exposing a target cell to a prolactin receptor antagonist and an agent that inactivates the HER2/neu signaling pathway.

8. The method of embodiment 7, wherein the prolactin receptor antagonist comprises an amino acid substitution at position 129.

9. The method of embodiment 7, wherein the agent that inactivates the HER2/neu signaling pathway is HERCEPTIN® (trastuzamab).

10. The method of embodiment 8 or 9, wherein the HERCEPTIN® (trastuzamab) is administered concurrently or sequentially with the prolactin receptor antagonist.

11. The method of embodiment 10, wherein the target cell is selected from the group consisting of a breast cancer cell that expresses a prolactin receptor and a prostate cancer cell that expresses a prolactin receptor.

12. The method of embodiment 8, wherein the amino acid at position 129 is substituted with arginine.

13. A method for slowing tumor growth comprising exposing a target cell to a prolactin receptor antagonist and an agent that inactivates the HER2/neu signaling pathway.

14. The method of embodiment 13, wherein the prolactin receptor antagonist comprises an amino acid substitution at position 129.

15. The method of embodiment 13, wherein the agent that inactivates the HER2/neu signaling pathway is HERCEPTIN® (trastuzamab).

16. The method of embodiment 14 or 15, wherein the HERCEPTIN® (trastuzamab) is administered concurrently or sequentially with the prolactin receptor antagonist.

17. The method of embodiment 16, wherein the target cell is selected from the group consisting of a breast cancer cell that expresses a prolactin receptor and a prostate cancer cell that expresses a prolactin receptor.

18. The method of embodiment 14, wherein the amino acid at position 129 is substituted with arginine.

The invention claimed is:

1. A method for inhibiting a breast cancer cell proliferation, inducing apoptosis in a breast cancer cell, or breast slowing tumor growth consisting of exposing a target breast cancer cell to a prolactin receptor antagonist and an agent that inactivates the HER2/neu signaling pathway, wherein the prolactin receptor antagonist is a human prolactin in which a glycine residue at position 129 is substituted with an arginine;

wherein said prolactin receptor antagonist interferes with the prolactin signaling pathway;

wherein said agent that inactivates the HER2/neu signaling pathway is an antibody against a HER2;

and wherein said target breast cancer cell expresses a prolactin receptor.

2. The method of claim 1, wherein the agent that inactivates the HER2/neu signaling pathway is trastuzamab.

3. The method of claim 2, wherein trastuzamab is administered concurrently or sequentially with the prolactin receptor antagonist.

* * * * *